United States Patent
Schroeder et al.

(10) Patent No.: US 9,989,472 B2
(45) Date of Patent: Jun. 5, 2018

(54) SOLUTION CATHODE GLOW DISCHARGE ELEMENTAL ANALYSIS

(71) Applicant: ALBERTA INNOVATES-TECHNOLOGY FUTURES, Edmonton (CA)

(72) Inventors: Stuart Garth Schroeder, Sherwood Park (CA); Theodore Meyer Garver, Edmonton (CA); Paul Peter Pastushak, Edmonton (CA)

(73) Assignee: InnoTech Alberta Inc., Edmonton (CA)

( * ) Notice: Subject to any disclaimer, the term of this patent is extended or adjusted under 35 U.S.C. 154(b) by 0 days. days.

(21) Appl. No.: 15/274,303

(22) Filed: Sep. 23, 2016

(65) Prior Publication Data

US 2017/0097304 A1 Apr. 6, 2017

Related U.S. Application Data

(60) Provisional application No. 62/232,041, filed on Sep. 24, 2015.

(51) Int. Cl.
| | |
|---|---|
| *G01J 3/30* | (2006.01) |
| *G01N 21/67* | (2006.01) |
| *G01N 21/69* | (2006.01) |
| *G01N 33/20* | (2006.01) |
| *G01J 3/44* | (2006.01) |

(52) U.S. Cl.
CPC ............. G01N 21/67 (2013.01); G01N 21/69 (2013.01); *G01J 3/44* (2013.01); *G01N 33/20* (2013.01)

(58) Field of Classification Search
CPC ........ G01N 21/67; G01N 21/69; G01N 21/68; G01J 3/30
See application file for complete search history.

(56) References Cited

U.S. PATENT DOCUMENTS

| | | | |
|---|---|---|---|
| 4,156,828 A | 5/1979 | Maisenhalder et al. | |
| 5,760,897 A | 6/1998 | Cserfalvi et al. | |
| 7,929,138 B1 | 4/2011 | Webb et al. | |
| 2005/0012038 A1* | 1/2005 | Marcus ..................... | G01J 3/10 250/288 |

(Continued)

FOREIGN PATENT DOCUMENTS

| | | |
|---|---|---|
| CN | 103163116 A | 6/2013 |
| CN | 104058480 B | 9/2014 |
| WO | 2007012904 A3 | 4/2007 |

OTHER PUBLICATIONS

Belchamber et al., "Correlation Study of Internal Standardization in Inductively Coupled Plasma Atomic Emission Spectrometry," Spectrochimica Acta Part B: Atomic Spectroscopy, May 1982, vol. 37(12), pp. 1037-1046.

(Continued)

*Primary Examiner* — Abdullahi Nur
(74) *Attorney, Agent, or Firm* — Borden Ladner Gervais LLP; Tim Webb

(57) ABSTRACT

A method and apparatus for solution cathode glow discharge (SCGD) elemental analysis. A solution-catching collar, in the form of a weir, a wicking element, or combinations thereof between the outlet tip of the capillary tube and the base of a grounding electrode tip maintain a solution sample level proximate the plasma emission region.

27 Claims, 29 Drawing Sheets

(56) References Cited

U.S. PATENT DOCUMENTS

2014/0151343 A1 6/2014 Foret

OTHER PUBLICATIONS

Bol'Shakov et al., "Laser Ablation Molecular Isotopic Spectrometry for Rare Isotopes of the Light Elements," Spectroscopy, Jul. 2014, vol. 29(6), pp. 30-39.
Broekaert et al., "Analytical Atomic Spectrometry with Flames and Plasmas," Verelag GmbH, Weinheim: Wiley-VCH2005.
Doroski et al., "Solution-Cathode Glow Discharge—Optical Emission Spectrometry of a New Design and Using a Compact Spectrograph," Journal of Analytical Atomic Spectrometry, May 2013, vol. 28, pp. 1090-1095.
Greda et al., "Comparison of performance of direct current atmospheric pressure glow microdischarges operated between a small sized flowing liquid cathode and a miniature argon or helium flow microjets," Journal of Analytical Atomic Spectrometry, Apr. 2013, vol. 28, pp. 1233-1241.
Motret et al., "Investigations of Silicon Oxide UV Emission in a Non-Thermal Atmospheric Plasma—Comparison with Synthetic Spectra," Journal of Physics D: Applied Physics, Aug. 2003, vol. 36, pp. 2060-2066.
Todoli et al., "Liquid Sample Introduction in ICP Spectrometry," Elsevier,2008.
Wang et al., "Design Modification of a Solution-Cathode Glow Discharge—Atomic Emission Spectrometer for the Determination of Trace Metals in Titanium Dioxide," Journal of Analytical Atomic Spectrometry, Jul. 2014, vol. 29, pp. 2042-2049.
Webb et al., "Compact Glow Discharge for the Elemental Analysis of Aqueous Samples," Analytical Chemistry, Sep. 2007, vol. 79, pp. 7899-7905.
Zhang et al., "Determination of Trace Heavy Metals in Environmental and Biological Samples by Solution Cathode Glow Discharge—Atomic Emission Spectrometry and Addition of Ionic Surfactants for Improved Sensitivity" Talanta, 2014, vol. 119, pp. 613-619.
International Search Report and Written Opinion of the International Searching Authority for Application No. PCT/CA2016/051121, dated Nov. 10, 2016, 8 Pages.

\* cited by examiner

SOLUTION CATHODE GLOW DISCHARGE ELEMENTAL ANALYSIS

CROSS REFERENCE TO RELATED APPLICATIONS

This application claims the benefit of priority of U.S. Provisional Patent Application No. 62/232,041 filed Sep. 24, 2015, which is hereby incorporated by reference.

FIELD

The present disclosure relates generally to elemental analysis of soluble species in aqueous solutions. More particularly, the present disclosure relates to elemental analysis of samples based on solution cathode glow discharge technology (SCGD).

BACKGROUND

Industrial processes requiring production of steam or other high temperature process fluids are subject to equipment fouling and scale formation issues. An example of one such process is the production of high-quality steam for SAGD (steam assisted gravity drainage) in the recovery of bitumen. The affected equipment may include, for example, water treatment operations, steam boilers, and once through steam generators (OTSG).

Deposition and scaling at heat exchange surfaces occurs because temperature, concentration, and pressure changes disrupt solubility equilibria to cause solids formation. Deposited substances are largely combinations of inorganic cations and inorganic and organic anions. The primary cations for scale formation are ions of Ca, Mg, Fe, and Mn. These cationic species combine with anionic species including $SiO_2$, $CO_3^{2-}$, $Cl^-$, and organic acids (humic and naphthalenic). Other elements that may contribute to fouling are Cu, Al, Na, Ba, Sr, K, Rb, Cs, and Li. Boiler fouling and scale formation may lead to significant costs due to losses in steam production efficiency and costly down-time. In spite of the importance of dissolved inorganic ions to boiler integrity, there is currently no on-line means of monitoring these metal ions at relevant concentrations for real-time process control.

Simultaneous multi-element analysis of metal ions is normally performed by lab-based techniques, such as inductively coupled plasma atomic emission spectrometry (ICP-AES). ICP-AES has never been adapted to on-line measurements because of high argon gas consumption and the requirement of frequent recalibrations due to instrument drift. However, a novel plasma spectrochemical technique has been described that does not consume inert gas and avoids instrument drift issues that plague traditional techniques. This technique is called solution cathode glow discharge (SCGD) and has shown linear calibration with detection limits in the low parts per billion range (see: Greda, K., et al., *Comparison of performance of direct current atmospheric pressure glow microdischarges operated between a small sized flowing liquid cathode and a miniature argon or helium flow microjets*, J. Anal. At. Spectrom., 28, 1233-1241 (2013) and Doroski, T. A., et al., *Solution-cathode glow discharge-optical emission spectrometry of a new design and using a compact spectrograph*. J. Anal. At. Spectrom., 2013. 28: p. 1090-1095). SCGD appears to be an ideal technique for simultaneous multi-element analysis of metal ions in on-line applications.

From the academic literature, a representation of the solution cathode glow discharge is shown in FIG. 1. This design has superior analytical performance and simplicity compared to previous published versions. The glass capillary extends 3 mm above the grounded graphite rod and the tungsten anode is 3 mm above the glass capillary. Electrical contact between the tip of the glass capillary and the graphite rod is made along the 3 mm vertical glass capillary by the liquid overflow of the solution cathode. Optimized electrical contact between the tip of the glass capillary and the graphite rod is made when the distance that the glass capillary extends above the graphite is minimized. However, distances less than 3 mm promote a glow-to-arc transition where the plasma anchors to the graphite rod as opposed to the tip of the glass capillary. Electrical arcing can destroy electrode components and prohibits the analytical performance of the instrument. Therefore, a compromised distance of 3 mm is used and 2.0 mL/min is the lowest sample flow rate that can be used before analytical performance degrades (see: Wang, Z., et al., *Design modifications of a solution cathode glow discharge atomic emission spectrometer for the determination of trace metals in titanium dioxide*. J. Anal. At. Spectrom., 2014. 00: p. 1-9 and Zhang, Z., et al., *Determination of trace heavy metals in environmental and biological samples by solution cathode glow discharge atomic emission spectrometry and addition of ionic surfactants for improved sensitivity*. Talanta, 2014. 119: p. 613-619). Lower flow rates degrade the analytical performance since the electrical connection through the fluid along the 3 mm glass capillary is degraded as flow rates decrease.

Within the patent literature, several variations of SCGD devices are disclosed. One of the earlier patents describing a SCGD device is U.S. Pat. No. 5,760,897 from Cserfalvi et al.; however, the inventors do not provide a proposed flow rate. Later patent application published WO/2007/012904, also from Cserfalvi et al. discloses a continuous flow rate of approximately 5-10 mL/min. China patent application CN 103163116 discloses the lowest flow rate achieved as 2.5 mL/min. U.S. Pat. No. 7,929,138 to Webb et al. discloses an SCGD configuration that facilitates analysis at low sample solution flow rates ranging from 2.0 to 3.0 mL/min. Although the inventors note that lower flow rates such as 1.5 mL/min. are also supported by the system, they disclose that their present method enables analysis between 2.0 and 2.5 mL/min. The flow rates in the Webb system are limited by the distance between the base of the plasma and the overflow solution in the reservoir in contact with the grounding electrode, which creates a greater resistance. There is therefore a need for an SCGD apparatus capable of flow rates below 2.0 mL/min that maintains a stable plasma emission and does not degrade the analytical performance.

To initiate the plasma in an SCGD device, a spark is required to jump the gap between the anode and flowing solution cathode and in the past this has been accomplished by one of two methods. Currently, the most common method is to physically lower the anode until it is within 1 mm of the cathode and then apply power from the dc power supply. At less than 1 mm distance, common dc power supplies have a sufficient voltage limit to jump the gap and initiate the plasma. Once the plasma is lit, the anode can be retracted to leave a 3 mm gap between electrodes. Thus, this method requires a mechanical mechanism to move the anode up and down, which has potential for wear and breakage. If the anode could be fixed in position, a simpler and more robust anode/cathode configuration can be built. Another method to initiate the plasma is to add a second high voltage power supply where the voltage, in excess of 10,000 V, is used solely to initiate the plasma by jumping the 3 mm gap between electrodes. This method runs the risk of damaging the main power supply that drives the plasma. There is therefore a need in the art for a method of initiating the plasma in SCGD that allows for a fixed configuration of the anode and cathode and does not require a second power supply.

To date, SCGD devices have primarily been used for the analysis of metal ions in aqueous solutions. Molecular emissions have been seen as background but SCGD devices have not been previously used for analysis of molecular species. Oxides, nitrides, and hydrides are classes of molecular species that can be formed in atmospheric pressure plasmas and can potentially be detected by molecular emission.

Isotopic analysis is an essential technique in the fields of medicine, chemistry, materials science, archeology, hydrology, carbon dating, and nuclear forensics. Traditionally, isotopic information has been determined by sophisticated isotope ratio mass spectrometers. Recently, laser ablation molecular isotopic spectrometer (LAMIS) has been used to provide isotopic analysis based on optical emission of molecular species. LAMIS has been shown to measure isotopes of hydrogen, boron, carbon, nitrogen, oxygen and chlorine (see: Bol'shakov, A. A., et al., *Laser ablation molecular isotopic spectrometry for rare isotopes of the light elements*. Spectroscopy, 2014. 29(6): p. 30-39). Although SCGD has not been previously disclosed for isotope measurement, isotopic analysis can be more practically accomplished using molecular spectra since the difference in isotopic masses has only a small effect on the electronic transitions in atoms, but a relatively large effect on the vibrational and rotational energy levels in molecules.

It is, therefore, desirable to provide improved apparatus and methods for SCGD.

SUMMARY

It is an object of the present disclosure to obviate or mitigate at least one disadvantage of previous apparatus and methods for SCGD.

The present disclosure provides a modified solution cathode glow discharge (SCGD) apparatus and methods to achieve stable plasmas at low sample flow rates with optimized emission for measurement of the elemental composition of dissolved substances in aqueous solutions by atomic emission spectrometry. The modified SCGD design provides a robust electrical connection to the plasma while reducing or preventing glow-to-arc transitions. As the solution sample flow rate decreases from 4.0 to 1.0 mL/min, the emission intensity of dissolved substances increases with a corresponding decrease in emission noise.

In a first aspect, the present disclosure provides a solution cathode glow discharge (SCGD) apparatus including an anode adapted to connect to a dc power source, the anode having an anode tip, a grounding electrode adapted to connect to the dc power source, the grounding electrode having a grounding electrode tip proximate the anode, the region proximate the grounding electrode tip and the anode tip forming a plasma emission region, a capillary tube adapted to receive a solution sample, the capillary tube having an outlet tip proximate the grounding electrode tip, and a solution-catching collar between the outlet tip of the capillary tube and a base of the grounding electrode tip, adapted to maintain a solution level proximate the plasma emission region.

In an embodiment disclosed, the solution-catching collar includes a circular weir.

In an embodiment disclosed, the SCGD apparatus further includes a circular bubble blocker, proximate the outlet tip of the capillary tube to prevent bubbles from directly entering the plasma emission region.

In an embodiment disclosed, the solution-catching collar includes a wicking element.

In an embodiment disclosed, the wicking element includes a glass frit wick or a porous ceramic wick.

In an embodiment disclosed, the wick is disk shaped.

In an embodiment disclosed, the wick is tapered, having a wick tip proximate the grounding electrode tip.

In an embodiment disclosed, the SCGD apparatus further includes an annular flow restrictor around the grounding electrode such that, in operation, a region of the grounding electrode is substantially covered by waste sample solution.

In an embodiment disclosed, the annular flow restrictor includes an O-ring or a secondary wicking element.

In an embodiment disclosed, the solution-catching collar is situated between about 0.3 and 3.0 mm below the outlet tip of the capillary tube.

In an embodiment disclosed, the anode and the grounding electrode are fixed, the distance between the anode tip and the grounding electrode tip set in advance of operation.

In an embodiment disclosed, the SCGD apparatus further includes a thermally conductive copper heat sink thermally connected with the anode to dissipate heat from the anode.

In a further aspect, the present disclosure provides a method of analyzing a solution sample including: providing a solution cathode glow discharge (SCGD) apparatus, providing the solution sample to a capillary tube of the SCGD apparatus at a sampling flow rate less than 2.0 mL/min, initiating or maintaining a stable plasma glow discharge by applying an electrical current, and analyzing the glow discharge emission.

In an embodiment disclosed, the method is used with a SCGD apparatus having an anode adapted to connect to a dc power source, the anode having an anode tip, a grounding electrode adapted to connect to the dc power source, the grounding electrode having a grounding electrode tip proximate the anode, the region proximate the grounding electrode tip and the anode tip forming a plasma emission region, a capillary tube adapted to receive a solution sample, the capillary tube having an outlet tip proximate the grounding electrode tip, and a solution-catching collar between the outlet tip of the capillary tube and a base of the grounding electrode tip, adapted to maintain a solution level proximate the plasma emission region.

In an embodiment disclosed, the method uses the SCGD apparatus wherein the solution-catching collar includes a circular weir.

In an embodiment disclosed, the method uses the SCGD apparatus wherein the solution-catching collar includes a wicking element.

In an embodiment disclosed, the method uses the SCGD apparatus further including an annular flow restrictor around the grounding electrode such that, in operation, a region of the grounding electrode is substantially covered by waste sample solution.

In an embodiment disclosed, the sampling flow rate is about 1.5 mL/min.

In an embodiment disclosed, the step of initiating the stable plasma glow discharge includes pulsing the solution sample at an initiation flow rate, the initiation flow rate greater than the sampling flow rate.

In an embodiment disclosed, the method further includes contacting an anode of the SCGD apparatus with the solution sample during the initiating.

In an embodiment disclosed, the method is conducted online or continuous or in a real-time environment.

In an embodiment disclosed, the step of analyzing the stable plasma glow discharge comprises applying a low pass filter to remove high frequency noise.

In an embodiment disclosed, the step of analyzing the stable plasma glow discharge emission comprises detecting one or more molecular species.

In an embodiment disclosed, the method further includes differentiating isotopes of the one or more molecular species.

In an embodiment disclosed, the one or more molecular species are dissolved silica or colloidal silica.

In a further aspect, the present disclosure provides a method of measuring colloidal counterions in an acidified solution sample containing clay, the method including providing a solution cathode glow discharge (SCGD) apparatus, providing an unfiltered solution sample to a capillary tube of the SCGD, initiating or maintaining a plasma glow discharge by applying an electrical current, and detecting at least the sodium glow discharge emission from the unfiltered solution sample, providing a filtered solution sample to the capillary tube, the filtered solution sample being substantially free from clay, initiating or maintaining a plasma glow discharge by applying an electrical current, and detecting at least the sodium glow discharge emission from the filtered solution sample, subtracting the sodium glow discharge emission of the filtered solution sample from the sodium glow discharge emission of the unfiltered solution sample to indicate a measure of clay counterions released by acidification.

In an embodiment disclosed, the net sodium glow discharge emission indicates a relative clay content of the solution sample.

In an embodiment disclosed, the method is used with a SCGD apparatus having an anode adapted to connect to a dc power source, the anode having an anode tip, a grounding electrode adapted to connect to the dc power source, the grounding electrode having a grounding electrode tip proximate the anode, the region proximate the grounding electrode tip and the anode tip forming a plasma emission region, a capillary tube adapted to receive a solution sample, the capillary tube having an outlet tip proximate the grounding electrode tip, and a solution-catching collar between the outlet tip of the capillary tube and a base of the grounding electrode tip, adapted to maintain a solution level proximate the plasma emission region.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides a method and system for solution cathode glow discharge elemental analysis.

Figure 1:
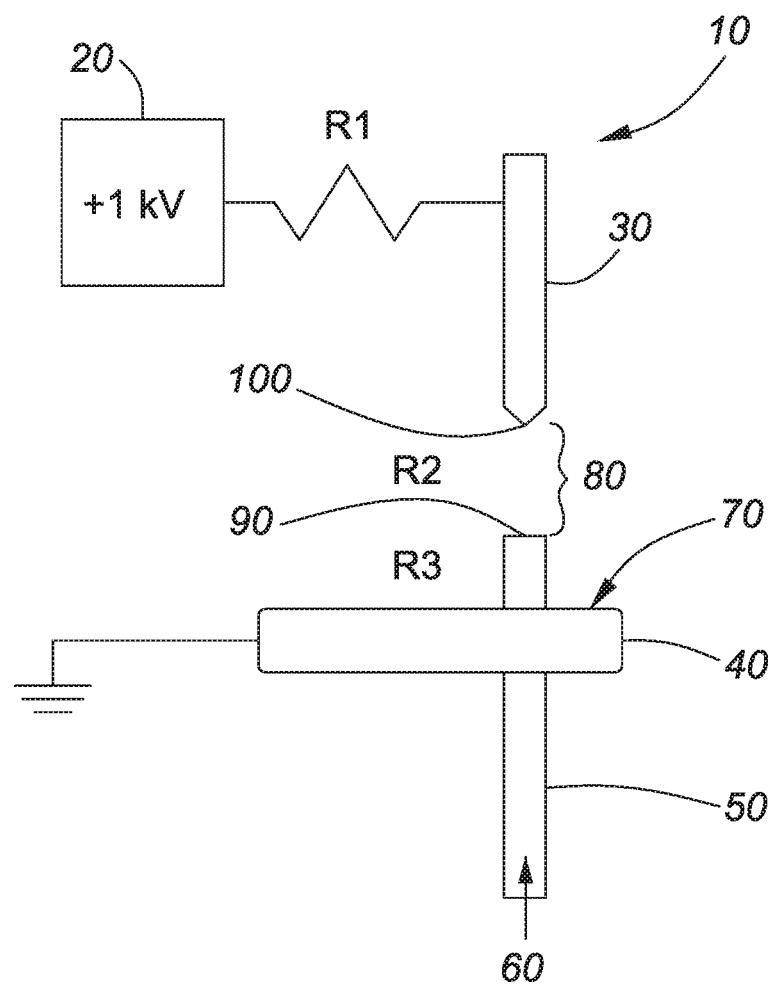
FIG. 1 is a schematic of a prior art solution cathode glow discharge (see: Doroski, T. A., et al.)

Referring to FIG. 1, a representation of a solution cathode glow discharge (SCGD) emission cell 10 found in the prior art is shown. A dc power source 20 connects to an anode 30 and a grounding electrode 40. The anode 30 may be, for example, a tungsten anode rod. The grounding electrode 40 may be, for example, a grounded graphite cathode rod. A capillary tube 50 delivers a solution sample 60 from a pump (not shown) proximate a top 70 of the grounding electrode 40. A plasma emission region 80 remains between an outlet tip 90 of the capillary tube 50 and a tip 100 of the anode 30. The capillary tube 50 may be, for example, a glass capillary tube. Upon activation of the power source 20, a plasma is formed in the plasma emission region 80.

The capillary tube 50 extends 3 mm above the top 70 of the grounding electrode 40, and the tip 100 of the anode 30 is 3 mm above the outlet tip 90 of the capillary tube 50. Electrical contact between the outlet tip 90 of the capillary tube 50 and the grounding electrode 40 is made along the 3 mm vertical capillary tube 50 by the overflow of the solution sample 60 from the outlet tip 90 of the capillary tube 50. Optimized electrical contact between the outlet tip 90 of the capillary tube 50 and the grounding electrode 40 is made when the distance that the capillary tube 50 extends above the grounding electrode 40 is minimized. However, distances less than 3 mm tend to promote a glow-to-arc transition where the plasma anchors to the grounding electrode 40 as opposed to the outlet tip 90 of the capillary tube 50. Electrical arcing can destroy electrode components and prohibits the analytical performance of the SCGD instrument. Therefore, typically a compromised distance of about 3 mm is used and 2.0 mL/min is the lowest flow rate for the solution sample 60 that can be used before analytical performance degrades.

Three different electrical resistance values are shown for a SCGD device found in the prior art. R1 is the ballast resistor 170 used to increase the output impedance of the dc power source 20 and limit the current delivered. R2 is the gas phase resistance of the plasma and R3 is the resistance of the electrical connection between the base of the plasma and the grounding electrode 40. This electrical connection is made through the overflow of acidified solution sample 60.

The incorporation of a solution-catching collar in the presently disclosed apparatus and methods significantly improves the operating characteristics of the solution cathode glow discharge (SCGD) emission cell found in the prior art. Reduction of R3 has been achieved by the insertion of a solution-catching collar in the form of a weir 110 (see FIGS. 2-4) or a wicking element 180 (see FIGS. 10-11, 50-51) between the tip 90 of the capillary tube 50 and the grounding electrode 40. The resistance of any material is directly proportional to its length and inversely proportional to its cross-sectional area. Therefore, placing a weir (110) or a wicking element 180 between the tip of the capillary tube 50 and the grounding electrode 40 increases the cross-sectional area of R3 and reduces the value of R3.

Solution-Catching Collar: Weir and Bubble Blocker Embodiment

Figure 2:
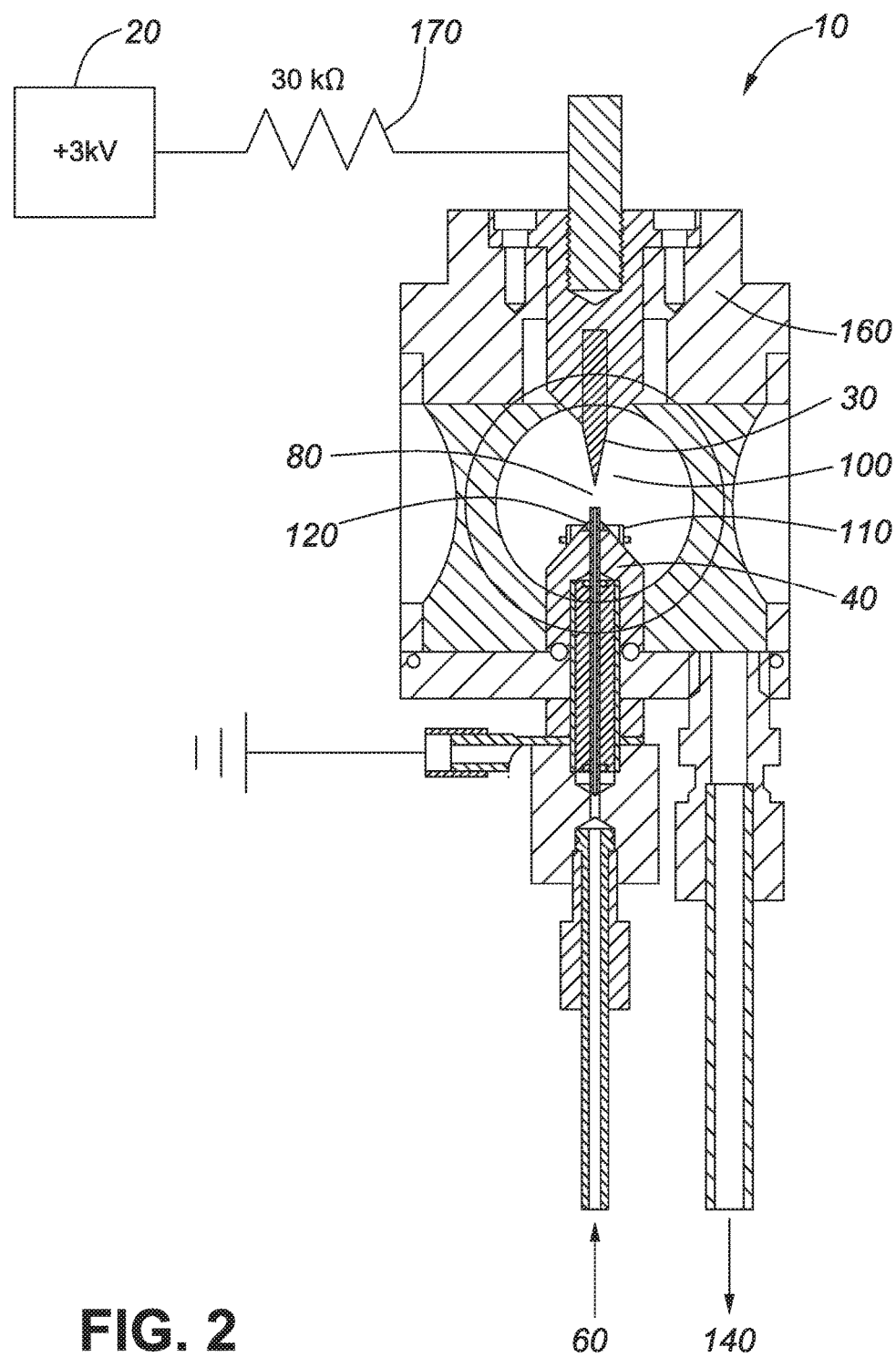
FIG. 2 is a schematic of a solution cathode glow discharge apparatus of the present disclosure, in a weir and bubble blocker embodiment.
Figure 3:
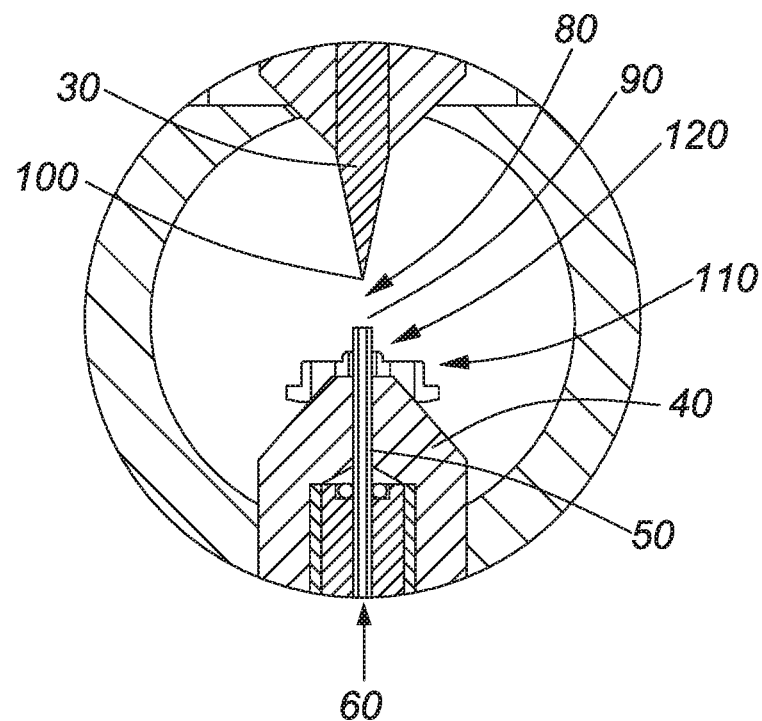
FIG. 3 is a close up of the solution cathode glow discharge apparatus of FIG. 2.
Figure 4:
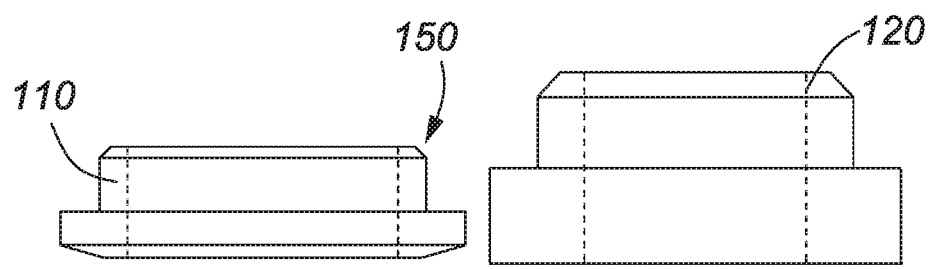
FIG. 4 are embodiments of a stainless steel weir (left) and a stainless steel bubble blocker (right), Swagelok part numbers SS-404-1 and SS-104-1 respectively of the present disclosure.

Referring to FIGS. 2-4, an embodiment of the SCGD emission cell 10 is shown. In an embodiment disclosed, the solution-catching collar is provided in the form of a weir 110. In an embodiment disclosed, the weir 110 is stainless steel. In an embodiment disclosed a bubble blocker 120 is also provided. In an embodiment disclosed, the bubble blocker 120 is stainless steel.

The weir 110 is placed within a low surface tension region of waste solution sample 140. The waste solution sample 140 has a sheeting action within this region and substantially uniformly spills over an upper side 150 of the weir 110, keeping the level of the solution sample 60 constant with respect to the outlet tip 90 of the capillary tube 50. In an embodiment disclosed, the capillary tube 50 is made of quartz, which is an inert material and has a higher melting point than glass. In alternative embodiments, the capillary tube 50 can be carbon nanotubes or graphite.

In an embodiment disclosed, the weir 110 raises the level of the solution sample 60 to within approximately 1.5 mm of the outlet tip 90 of the capillary tube 50. Raising this level has the effect of reducing the electrical resistance between the outlet tip 90 of the quartz capillary tube 50 and the grounding electrode 40. Electrical measurements were made in a constant voltage mode with and without the weir 110 and the bubble blocker 120. At the same applied voltage, the current was 65 mA without the weir 110 and the bubble blocker 120 and 74 mA with the weir 110 and the bubble blocker 120. This represents a reduction in electrical resistance of 3776Ω when the weir 110 and the bubble blocker 120 are in place. The weir 110 and the bubble blocker 120 are simply placed on top of the grounding electrode 40 as shown in FIGS. 2 and 3. The weir 110 leaves a thin layer of solution sample 60 covering the top of the grounding electrode 40 and the bubble blocker 120. This solution sample covering removes any electrical "hot spots" where a glow-to-arc transition can be initiated if the solution sample layer were absent. In an embodiment disclosed the height of the weir 110 may be increased, and in an embodiment disclosed the weir 110 is raised towards the outlet tip 90 of the quartz capillary tube 50.

In an embodiment disclosed, the anode 30 is made from a ⅛" tungsten carbide welding electrode ground to a point at the tip 100 with a 20 degree angle. Thermal management of the tungsten carbide anode 30 is achieved by placing the base of the anode 30 into thermally conductive copper heat sink 160. This prevents the anode 30 from overheating and has been shown to improve plasma stability (see: U.S. Pat. No. 4,156,828, Maisenhalder et al., Glow Discharge Apparatus And A Method Of Operating Same, 1979). The grounding electrode 40 was made from copper and was passivated by coatings of electroless nickel and gold. The output impedance of the dc power source 20 was increased with the use of ballast resistors 170. The ballast resistors were a series connection of up to six 5 kΩ wire wound power resistors for a maximum ballast resistance of 30 kΩ. A maximum ballast resistance of 30 kΩ would require a dc voltage of +3 kV. Alternatively, at a ballast resistance of 15 kΩ, a dc voltage of +2 kV could be used. Each resistor was mounted on a high efficiency heat-pipe heat sink with forced-fan cooling to keep the resistor at ambient temperature preventing drift. The glow-to-arc transition is inhibited with the use of a ballast resistor. The plasma was powered by a dc power supply, with appropriate supply of voltage and current, for example Glassman model PS/EW03R200-115 with a stability of 0.01% per hour after 0.5 hour warm-up, 0.05% per 8 hours. The plasma was created between the 3.0 mm gap between the capillary tube 50 and the tip 100 of the anode 30. For routine analytical work, the image of the plasma will be focused onto the entrance slit of a spectrometer (not shown). In an embodiment disclosed, the quartz capillary tube 50 delivering the flowing solution sample 60 to the plasma emission region 80 has an outside diameter of 1.0 mm, and an inside diameter of 0.5 mm. The flow of the solution sample 60 of between 1.0 to 3.5 mL/min was provided with a pulseless or pulse dampening pump, for example Valco Instruments model M50 pump (not shown). This pump can control flow from between 1 μL/min to 25 mL/min. The solution sample 60 is acidified prior to entry into the pump, for example in 0.1M $HNO_3$. In alternative embodiments, the solution sample 60 could be prepared in hydrochloric acid, sulfuric acid, or another suitable acid. The waste solution sample 140 was removed from the SCGD emission cell 10 by gravity drainage.

In operation a pump (not shown) supplies the sample solution 60 to the outlet tip 90 via the capillary tube 50. The sample solution 60 flows over bubble blocker 120 and the solution-catching collar in the form of the weir 110, down the side of the grounding electrode 40 and the waste solution sample 140 disposed of. Upon application of the dc power source 20, plasma is generated in the plasma emission region 80 and the emissivity of the plasma analyzed.

Test Setup

Unless otherwise stated, stability of the SCGD was determined at a flow rate of 1.5 mL/min and the solution sample 60 was made in 0.1M $HNO_3$.

All spectral data was acquired with an Oriel 77200 0.25 m scanning monochromator (unless otherwise stated), a 1200 line/mm grating was used for all spectral acquisitions greater than 589 nm and a 2400 line/mm grating for acquisitions below 589 nm. A Mightex TCE-1304-U CCD line camera was mounted at the exit focal plane of the monochromator, using a Toshiba 3648 pixel CCD (TCD1304DG) with a pixel size of 8×200 μm.

Stability of Plasma Emission

Figure 5:
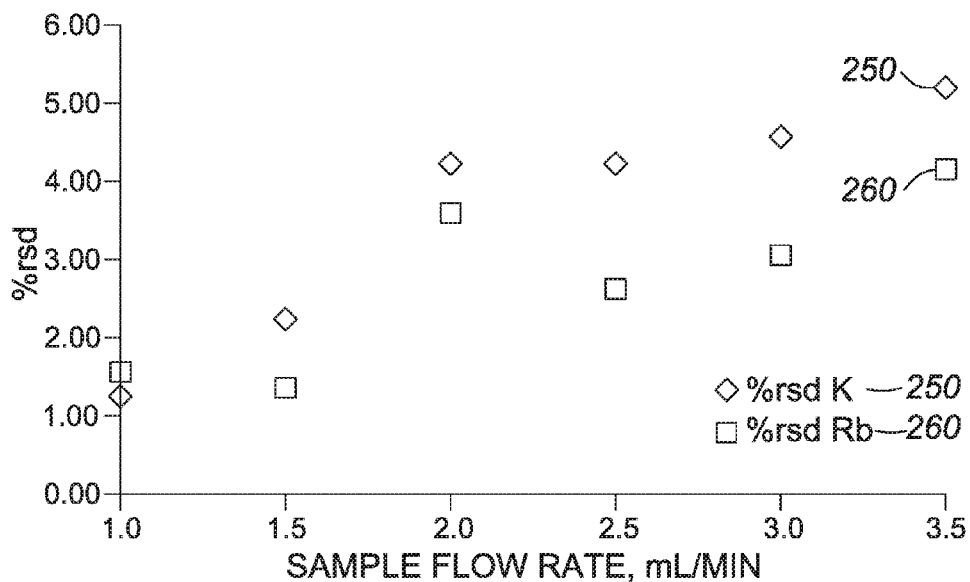
FIG. 5 is a graph of emission stability of K and Rb at 10 mg/L as measured with % rsd with sample flow rate.

Referring to FIG. 5, the effect of the flow rate of the solution sample 60 on emission stability from dissolved K (250) and Rb (260) at 10 mg/L is shown. Higher flow rates result in a decrease in emission stability and stability is optimized at a flow rate of 1.0 mL/min.

The long term percent relative standard deviation (% rsd) determined over a period of 2.3 hours with 4038 consecutive data acquisitions was calculated to be 0.6% for Li. The short term % rsd measured with 16 consecutive data acquisitions was calculated to be 0.05% for Li. For comparative purposes, the short term % rsd of published values for the SCGD are 1-2% rsd (see: Webb, M. R., et al., *Compact glow discharge for the elemental analysis of aqueous samples*. Anal. Chem., 2007. 79: p. 7899-7905), 0.6-7% rsd (see: Doroski, T. A., et al.), and better than 5% rsd (see: Greda, K. et al.) when the number of measurements ranged only from 5 to 10 over a time period of a few minutes at most. Also, the stability data from this current study compares very favorably to the lab-based technique of inductively coupled plasma atomic emission spectrometry (ICP-AES) where short term % rsd values can range from 1-2%, (see: Belchamber, R. M. and Horlick G., *Correlation study of internal standardization in inductively coupled plasma atomic emission spectrometry.* Spectrochimica Acta Part B, 1982. 37(12): p. 1037-1046 and Broekaert, J. A., *Analytical Atomic Spectrometry with Flames and Plasmas* 2005, Verelag GmbH, Weinheim: Wiley-VCH) and are considered satisfactory when they are <1% (see: Todoli, J.-J. and Mermet, J. M., *Liquid Sample Introduction in ICP Spectrometry* 2008: Elsevier).

Emission Intensity

Figure 6:
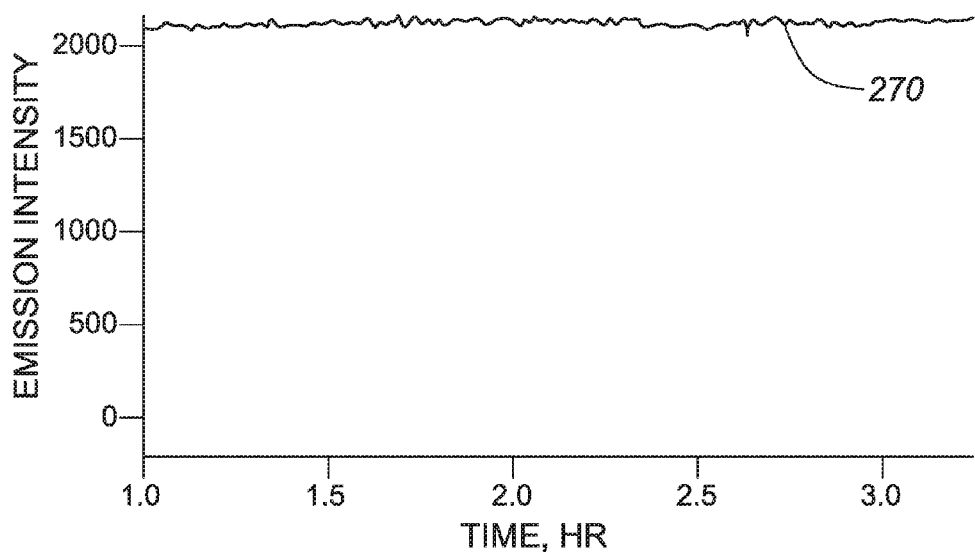
FIG. 6 is a graph of emission intensity, indicating long term stability of SCGD emission source from 7.5 ppm Li, 1 s integration time, low pass digitally filtered. Long term stability of 0.6% rsd between 1 and 3.3 hours. Short term stability of 0.05% rsd over 16 consecutive points.

Referring to FIG. 6, optical measurements of emission intensity 270 were made with an Ocean Optics SD2000 covering the visible to near-IR portion of the spectrum (grating 600 lines/mm, blazed at 500 nm, 25 um slit, OFLV-3, 2048 pixel CCD Sony 1LX511, 42 mm focal length, resolution FWHM 1.4 nm). A 1.0 second integration time was used.

Sensitivity of Plasma Emission

Figure 7:
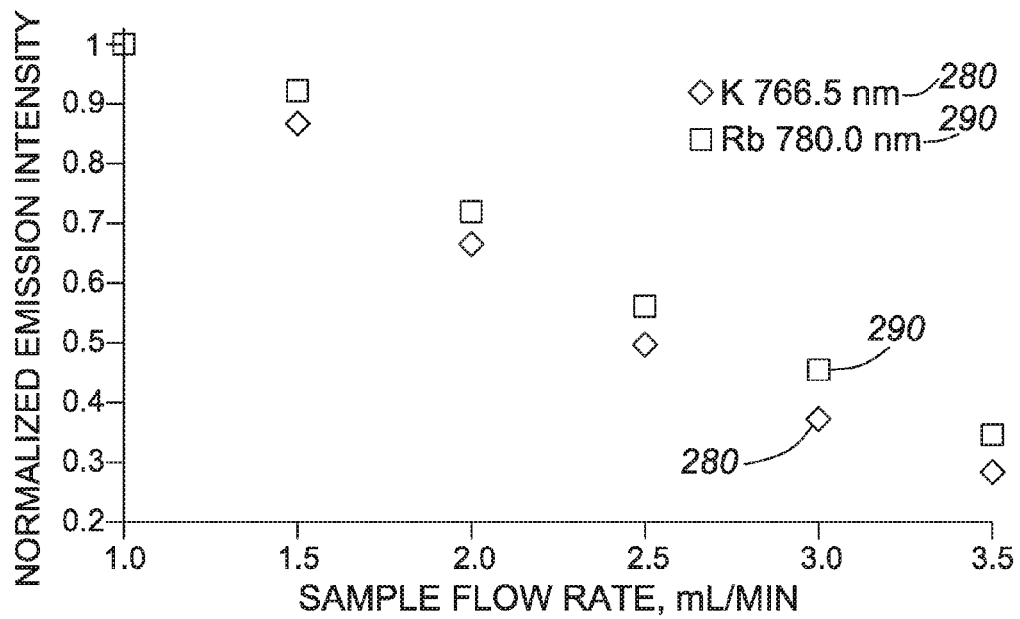
FIG. 7 is a graph of normalized emission intensity, indicating the effect of emission intensity of K and Rb at 10 mg/L with sample flow rate.

Referring to FIG. 7, the effect of the flow rate of the solution sample 60 on emission intensity from dissolved K (280) at 766.5 nm and Rb (290) at 780.0 nm at 10 mg/L is shown. Higher flow rates result in a decrease in emission intensity and emission intensity is optimized at a flow rate of about 1.0 mL/min.

Reduced Sample Flow Rates

Figure 8:
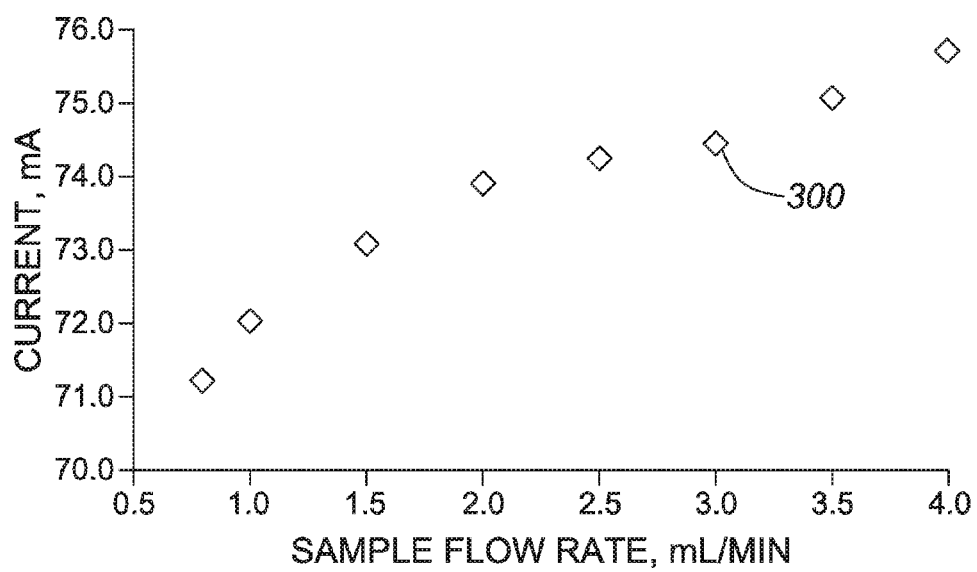
FIG. 8 is a graph of current, indicating the effect of sample flow rate on current while operating the power supply in the constant voltage mode.
Figure 9:
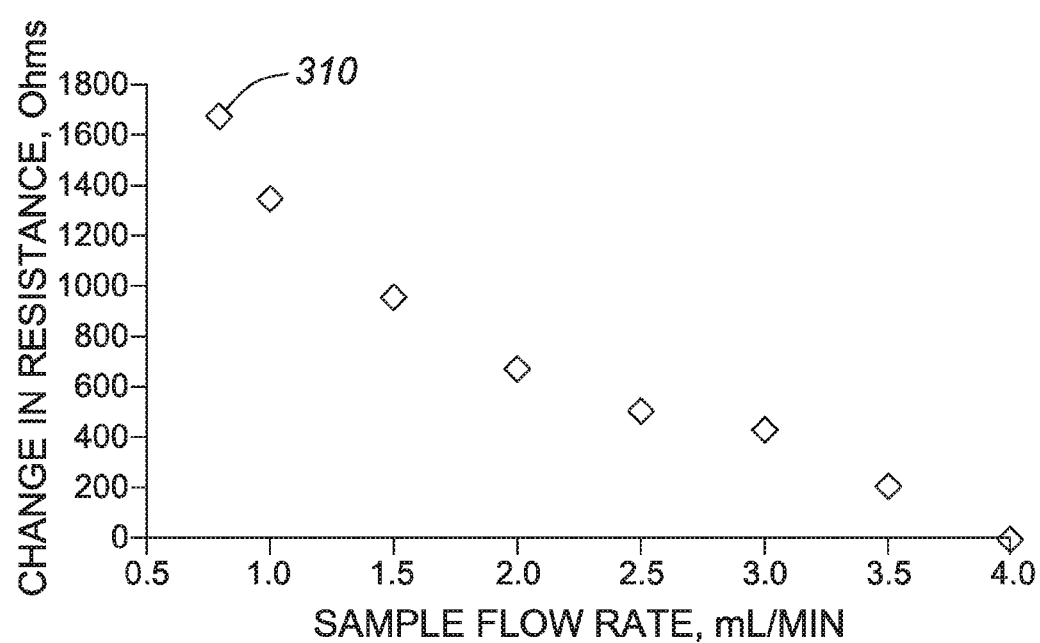
FIG. 9 is a graph of change in resistance, indicating a decrease in electrical resistance as the sample flow rate increases.

Referring to FIGS. 8 and 9, the effect of the flow rate of the solution sample 60 on current 300 and electrical resistance 310 is shown. These measurements were taken with the weir 110 and the bubble blocker 120 in place. It is clear that a higher flow rate favors improved electrical contact between the outlet tip 90 of the quartz capillary tube 50 and the grounding electrode 40. This occurs because a higher flow rate produces a thicker conduit of waste sample solution 140 and facilitates less resistance to current.

Optimized conditions will occur at low flow rates that promote signal intensity and stability. If flow rates are reduced too far, degradation of the electrical contact between the outlet tip 90 of the capillary tube 50 and the grounding electrode 40 will occur.

In addition to higher emission intensity, reduced sample flow rates are desirable in terms of lower total sample and acid consumption. For example, for an online industrial process control application, the solution sample 60 will be diluted and acidified prior to being introduced into the SCGD. Acid, from an acid reservoir, would be added to and mixed with the sample stream. If the total sample flow to the SCGD is 1.0 mL/min and the sample dilution factor is 10:1, the flow from the acid reservoir would be 0.9 mL/min. This works out to acid consumption of 1.3 L/day, 9.1 L/week, and 36.3 L/month. The frequency of acid refilling is reduced with a lower sample flow rate.

Of note, solution sample 60 flow rates than 1.0 mL/min are predicted to be possible, potentially as low as 0.5 mL/min at which point the electrical connection would likely be lost.

Solution-Catching Collar: Wicking Element Embodiment

Figure 10:
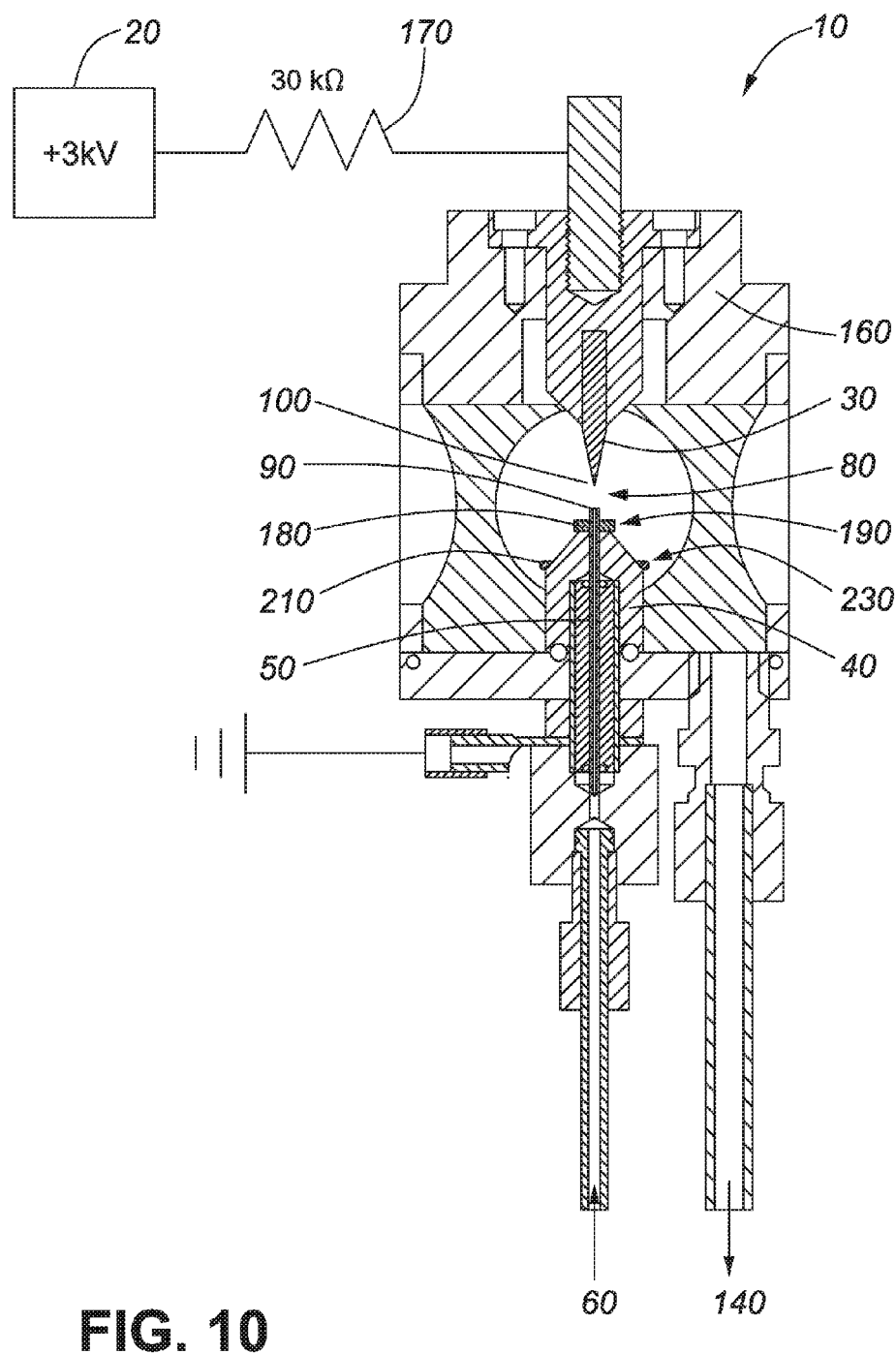
FIG. 10 is a schematic of a solution cathode glow discharge apparatus of the present disclosure, in a glass frit disk wicking element embodiment.
Figure 11:
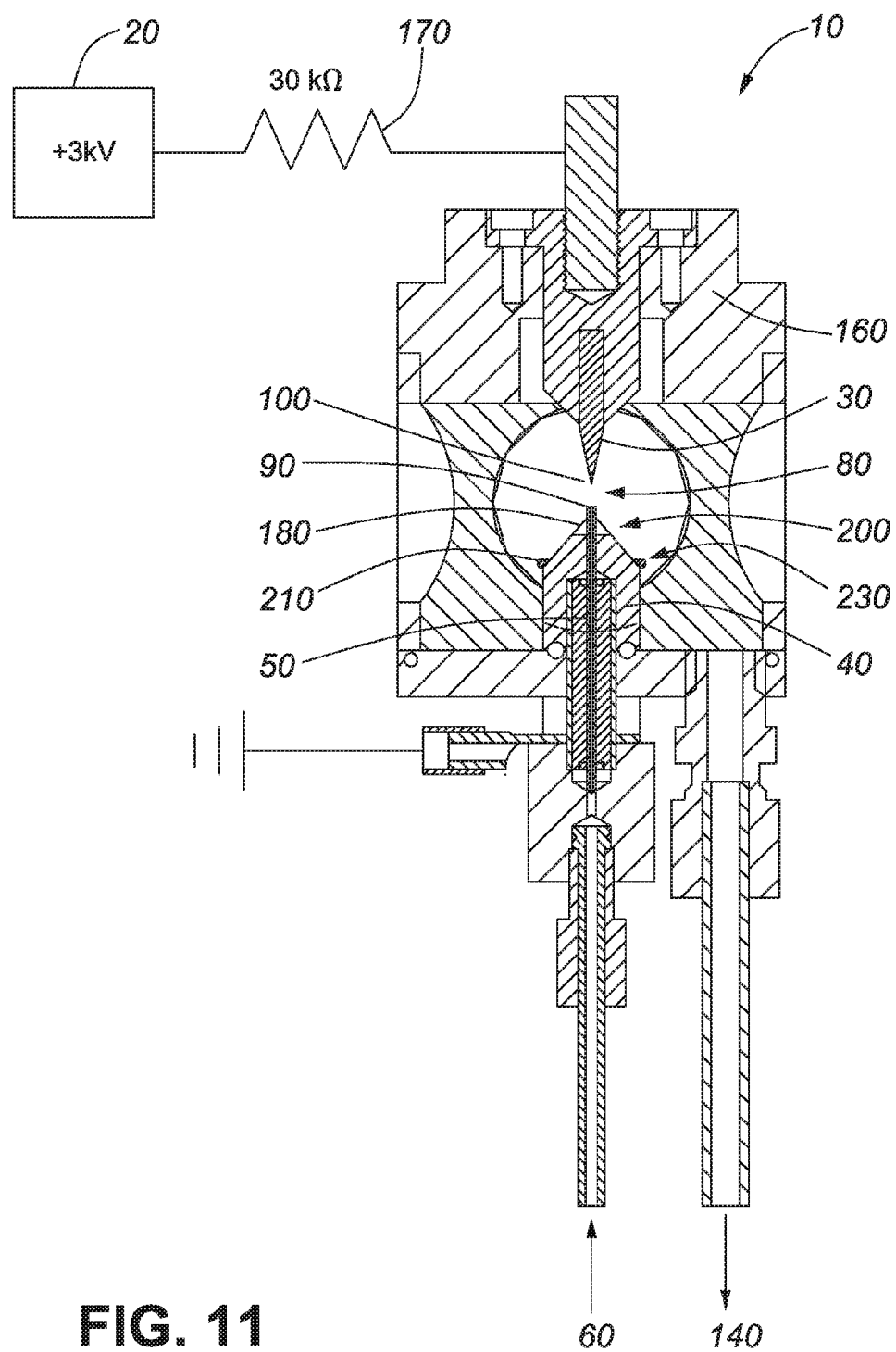
FIG. 11 is a schematic of a solution cathode glow discharge apparatus of the present disclosure, in a tapered porous ceramic wicking element embodiment.

Referring to FIGS. 10 and 11, in an alternative embodiment disclosed, a solution-catching collar in the form of a wicking element 180 is provided between the outlet tip 90 of the quartz capillary tube 50 and the grounding electrode 40. The wicking element 180, for example fabricated from either a glass frit disk wick 190 or a tapered porous ceramic wick 200, provides a robust electrical connection to the plasma while preventing glow-to-arc transitions. In an embodiment disclosed an annular flow restrictor 210 is provided between the wicking element 180 and a base 220 of the grounding electrode 40. In an embodiment disclosed the annular flow restrictor 210 is an O-ring 230 or a second wicking element 240 (see FIGS. 50-51).

The incorporation of a wicking element 180 between the outlet tip 90 of the capillary tube 50 and the grounding electrode 40 significantly improves the operating characteristics of the solution cathode glow discharge (SCGD) emission cell 10. The wicking element 180 can be made from a variety of materials and shapes and the two materials and shapes investigated were the glass frit disk wick 190 and the tapered porous ceramic wick 200. The tapered porous ceramic wick 200 provided better operational characteristics than the glass frit disk wick 190. Machinable porous ceramic is available in a variety of porosities and strengths. Other porous materials including chamotte brick and porous glass are also feasible as wicking elements. Alternatively, the wicking element could be fabric or cloth, for example polyester fabric, ceramic cloth and carbon fibre cloth.

In operation a pump (not shown) supplies the sample solution 60 to the outlet tip 90 via the capillary tube 50. The sample solution 60 flows over the wicking element 180 (glass frit disk wick 190 in FIG. 10 and tapered porous ceramic wick 200 in FIG. 11), down the side of the grounding electrode 40, over the annular flow restrictor 210 in the form of the O-ring 230, and the waste solution sample 140 disposed of. Upon application of the dc power source 20, plasma is generated in the plasma emission region 80 and the emissivity of the plasma analyzed.

Figure 50:
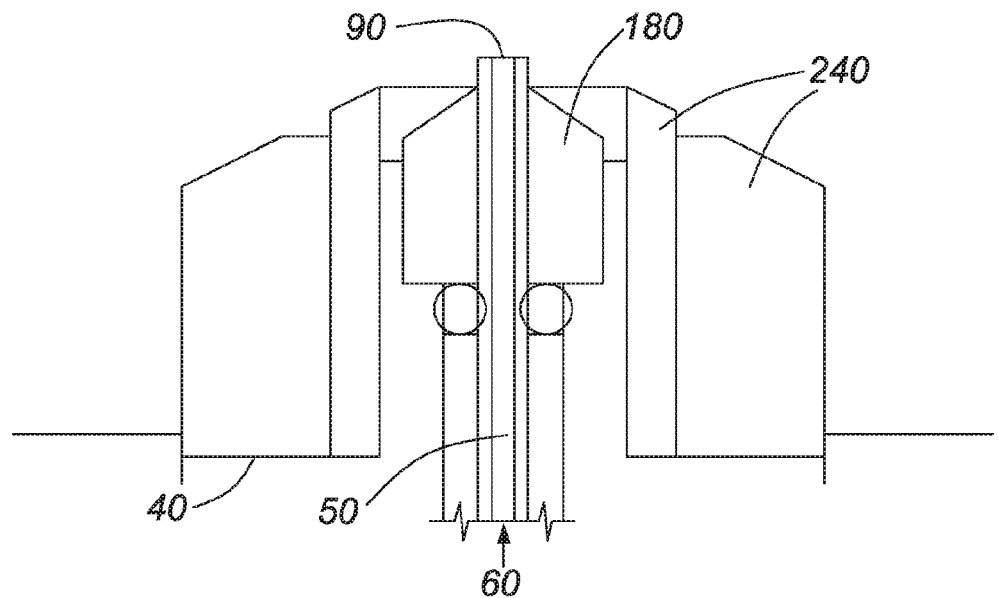
FIG. 50 is a schematic of a grounding electrode of a solution cathode glow discharge apparatus of the present disclosure, in a wicking element and a secondary element configuration.
Figure 51:
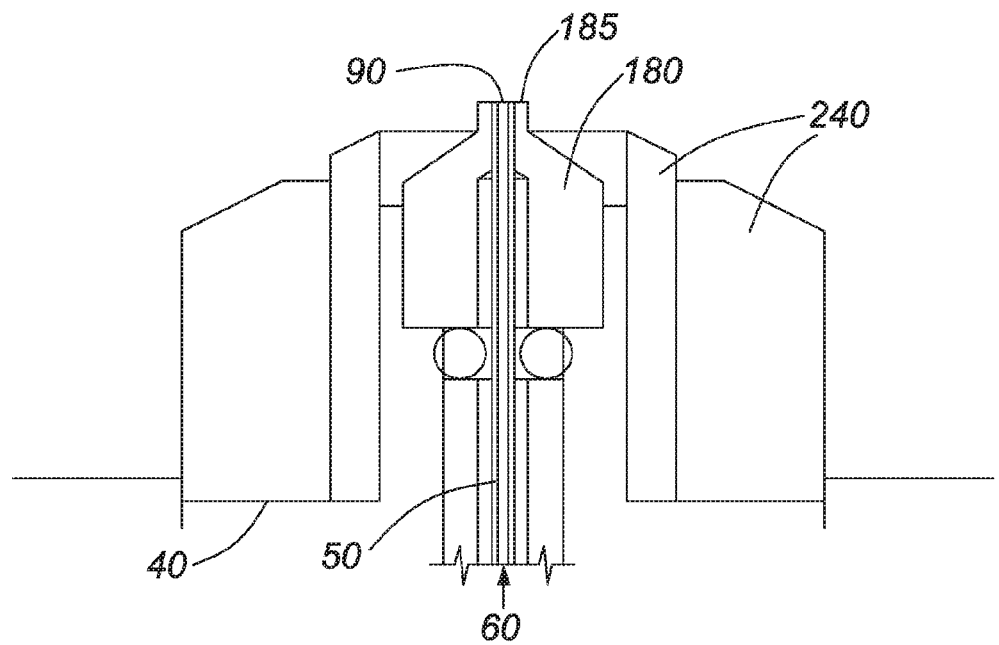
FIG. 51 is a schematic of a grounding electrode of a solution cathode glow discharge apparatus of the present disclosure, in a flush wicking element configuration.

Referring to FIGS. 50 and 51, in an embodiment disclosed, a secondary wicking element 240 may be used in addition to the wicking element 180. The wicking element 180 and the secondary wicking element 240 are machined from porous ceramic. The wicking element 180 reduces the electrical resistance between the outlet tip 90 of the quartz capillary tube 50 and the grounding electrode 40. The secondary wick 240 is an embodiment of the annular flow restrictor 210. The secondary wicking element 240 removes electrical hot spots and helps prevent a glow-to-arc transition. The secondary wicking element 240 is also used to maintain a consistent level of solution sample 60 with respect to the wicking element 180. The secondary wicking element 240 may comprise either one or two pieces of machinable porous ceramic. Referring to FIG. 51, in an embodiment disclosed, the wicking element 180 may have a wicking element tip 185 which is substantially flush with the outlet tip 90 of the quartz capillary tube 50. It is predicted that this design will provide an additional reduction of electrical resistance since the current will be conducted entirely over a porous and hydrophilic wick. This reduction in electrical resistance is predicted to further improve the stability of the plasma and enable longer-term unattended use.

In operation a pump (not shown) supplies the sample solution 60 to the outlet tip 90 via the capillary tube 50. The sample solution 60 flows over the wicking element 180, and over the annular flow restrictor 210 in the form of secondary wicking element 240, and the waste solution sample 140 disposed of. Upon application of the dc power source 20, plasma is generated in the plasma emission region 80 and the emissivity of the plasma analyzed.

Stability of Electrical Contact to the Plasma

Figure 12:
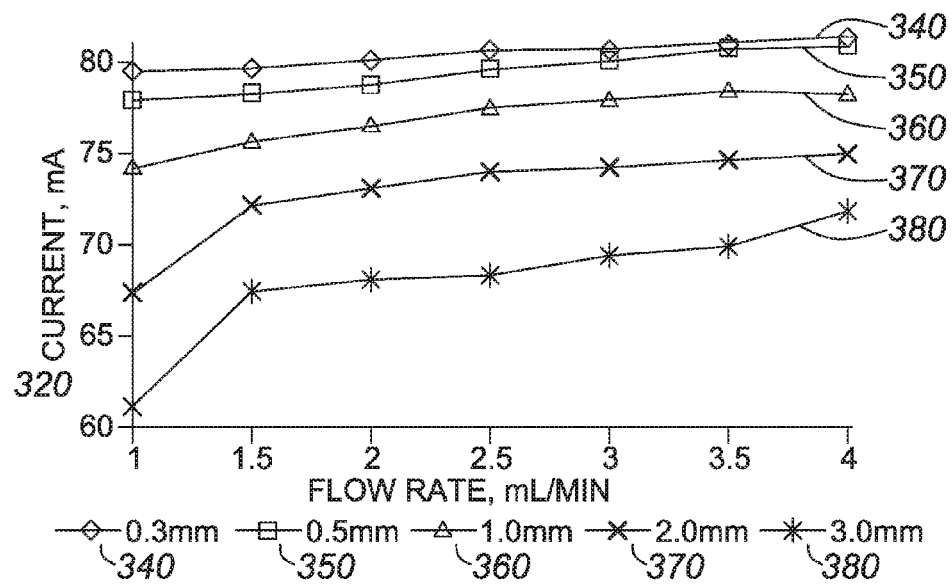
FIG. 12 is a graph of current, indicating current measurements with sample solution flow rates of 1.0-4.0 mL/min taken with quartz capillary tube lengths of 0.3-3.0 mm above the wicking element. The tube length of 0.3 mm was with the tapered porous ceramic wick and all others were with the glass frit disk wick.
Figure 13:
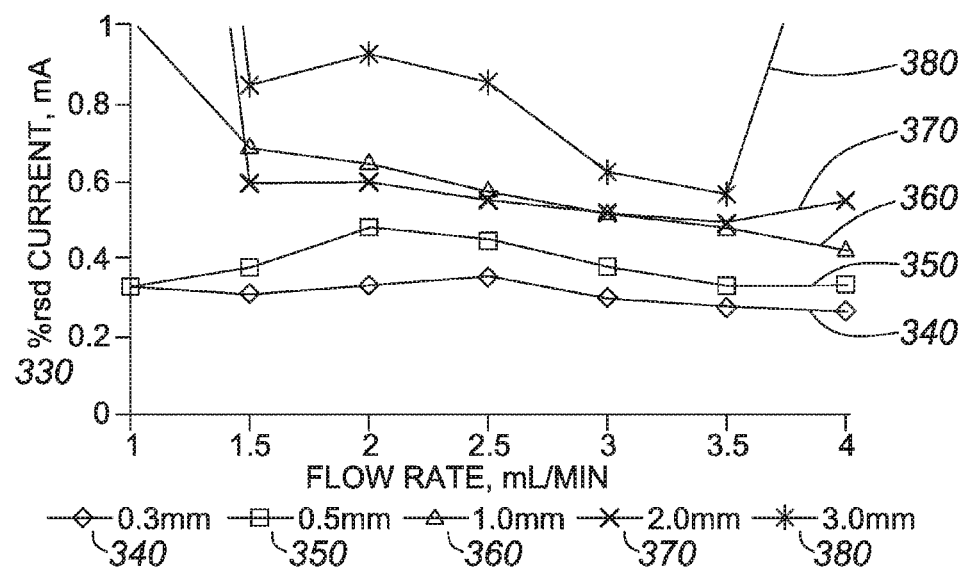
FIG. 13 is a graph of noise in the current measurements represented as % rsd with sample solution flow rates of 1.0-4.0 mL/min taken with quartz capillary tube lengths of 0.3-3.0 mm above the wicking element. The tube length of 0.3 mm was with the tapered porous ceramic wick and all others were with the glass frit disk. Data collected at 1.67 kHz, 10,000 points.

Referring to FIGS. 12 and 13, the electrical operating characteristics of the SCGD emission cell 10 of FIGS. 10 and 11 are shown (see FIG. 12 current 320 and FIG. 13 % rsd current 330) at solution sample 60 flow rates of 1.0-4.0 mL/min taken with quartz capillary tube heights of between 0.3-3.0 mm above the wicking element 180 (with 0.3 mm height marked 340, 0.5 mm marked 350, 1.0 mm marked 360, 2.0 mm marked 370, and 3.0 mm marked 380). The dc power source 20 was operated in the constant voltage mode with a voltage set to 2046.6 V and the current 320 allowed to float with changes in resistance. The tube length of 0.3 mm was with the tapered porous ceramic wick 200 and all others were with the glass frit disk wick 190.

There are at least two different types of plasma instabilities. The first type is catastrophic and is termed the glow-to-arc transition. It is marked by a significant rise in the plasma current and results in immediate failure of the device caused by melting of components under the high thermal loads. The glow-to-arc transition has been observed when using a quartz capillary tube 50 with the outlet tip 90 a distance of 1 mm above the grounding electrode 40 without the use of a wicking element 180. Greater distances above the grounding electrode 40 assist in preventing this type of failure. Removal of electrical "hot spots" also assists in preventing this type of failure. Hot spots are removed in the present design by providing a continuously wetted surface through the use of the wicking element 180 and the O-ring 230 shown in FIGS. 10 and 11. The second type of plasma instability occurs when the plasma anchors itself to multiple locations, other than the tip of the quartz capillary tube, directly on the wicking element 180. Since the plasma is extended over greater distances by anchoring itself to the wicking element 180, the plasma resistance increases. This increase in plasma resistance correlates with a decrease in plasma current when the dc power source 20 is operated in a constant voltage mode. This was observed and is shown at a flow rate of 1.0 mL/min with a quartz capillary tube distance of 2.0 and 3.0 mm above the wicking element 180. A significant decrease in current along with a marked increase in the current noise is shown in FIGS. 12 and 13 when the plasma partially anchors to the wicking element 180.

Referring to FIGS. 12 and 13, the effect of lowering the distance that the outlet tip 90 of the sample tube 50 extends above the wicking element 180 is graphically represented. The resistance, R3 between the outlet tip 90 (of the capillary tube 50) and the wicking element 180, is inversely proportional to the distance that the outlet tip 90 of the quartz capillary tube 50 extends above the wicking element 180, and as R3 is reduced there is a corresponding increase in current. This is clearly shown in FIG. 12. The noise in the current is graphically shown in FIG. 13 and is represented as the % rsd value at different sample flow rates and quartz capillary tube lengths above the wicking element 180. The noise in the current is directly related to the fluctuations in the value of R3. It is clear to see that quartz capillary tube heights of 0.3 and 0.5 mm provide the lowest noise values. A robust electrical connection to the base of the plasma will be seen when the fluctuations in the R3 value are the smallest. With an appropriate wicking element 180, for example a disk shaped glass frit 190 or a tapered porous ceramic 200, a robust electrical connection can be made while reducing the sample flow rate to 1.0 mL/min.

Stability of the Plasma Emission

Figure 14:
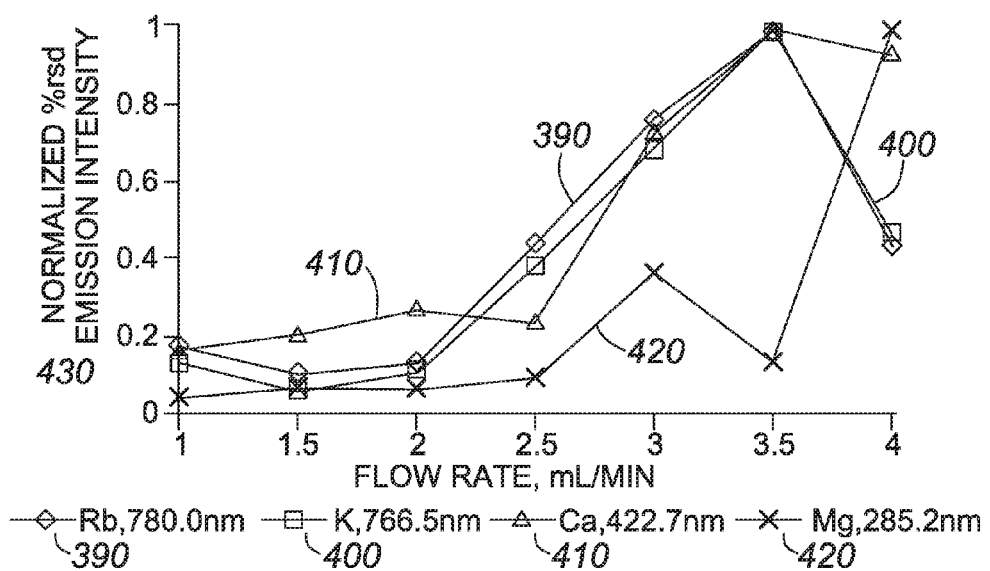
FIG. 14; is a graph of normalized % rsd values for emission intensity from Rb, K, Ca, and Mg for flow rates ranging from 1.0 to 4.0 mL/min.

Referring to FIG. 14, improved emission stability for Rb at 780.0 nm (390), K at 766.5 nm (400), Ca at 422.7 nm (410), and Mg at 285.2 nm (420) was observed as the sample flow rate is reduced to 1.0-2.0 mL/min. As already stated, emission intensity (% rsd emission intensity 430 shown) is optimized at a flow rate of 1.0 mL/min and we see from FIG. 14 that emission stability is also optimized in this flow rate range. The data from FIG. 14 was collected with the tapered porous ceramic wick 200 with the quartz capillary tube 50 extending only 0.3 mm above the wicking element 180.

Sensitivity of Plasma Emission

Figure 15:
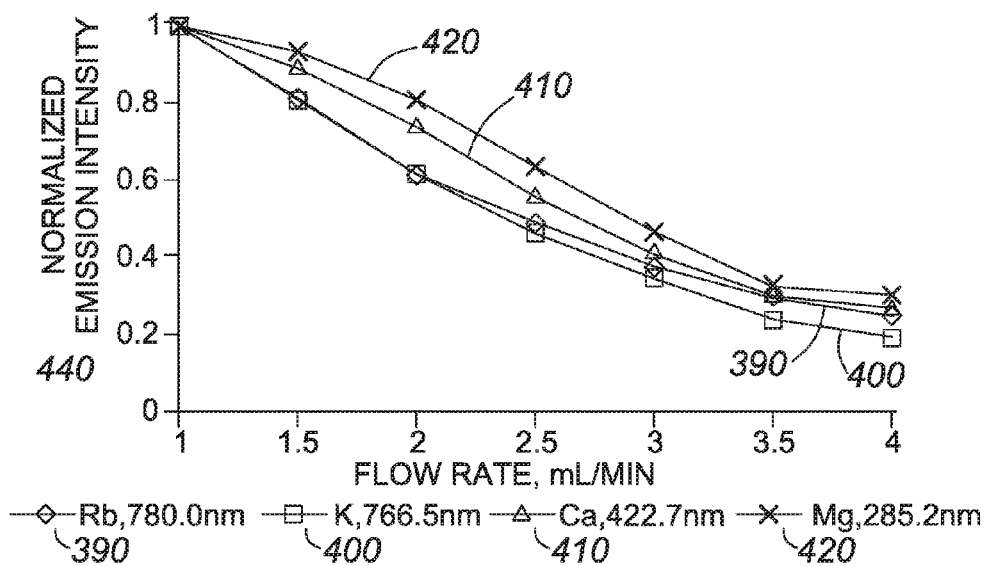
FIG. 15 is a graph of normalized emission intensity for Rb, K, Ca, and Mg for sample flow rates ranging from 1.0 to 4.0 mL/min.

Referring to FIG. 15, improved emission intensity for Rb at 780.0 nm (390), K at 766.5 nm (400), Ca at 422.7 nm (410), and Mg at 285.2 nm (420) was observed as the sample flow rate was reduced from 4.0 mL/min to 1.0 mL/min. Higher emission intensity will be directly related to lower detection limits. This improvement in emission intensity was observed across the spectrum from the ultraviolet through the visible and near infrared. It is assumed that all emission intensity from all elements will be improved at lower flow rates. The data from FIG. 15 was collected with the tapered porous ceramic wick 200 with the quartz capillary tube 50 extending only 0.3 mm above the wicking element 180. The data shown here (normalized emission intensity 440 shown) is a marked improvement over what is shown in the academic literature when emission intensity is optimized at a flow rate of 2.0 mL/min and is degraded at lower flow rates.

Reduced Sample Flow Rates

As already stated, the lowest sample flow rate in the academic literature for the SCGD is 2.0 mL/min without the use of a wicking element 180. With a wicking element 180, the sample flow rate can be reduced to 1.0 mL/min while still maintaining a more robust electrical contact to the plasma. As described above with regards to the weir 110 and the bubble blocker 120 embodiment, reduced sample rates are desirable in terms of lower total sample and acid consumption.

Plasma Initiation by Pulsing the Sample Delivery Pump

In a further aspect of the present disclosure, a novel method for initiating the plasma is provided by momentarily pulsing the flow rate of the solution sample 60 by pulsing the sample delivery pump (not shown) to drive the conductive solution sample 60 from the quartz capillary tube 50 and into the anode 30. When the power source 20 is turned on in advance of the pump pulse, a stable plasma is generated. Pulsing the sample delivery pump to initiate the plasma is an advancement compared to methods previously used since the anode 30 and the grounding electrode 40 can be fixed in position allowing for a simpler construction. Also, this method does not require a high voltage power supply that may damage the main power plasma power supply.

Figure 16:
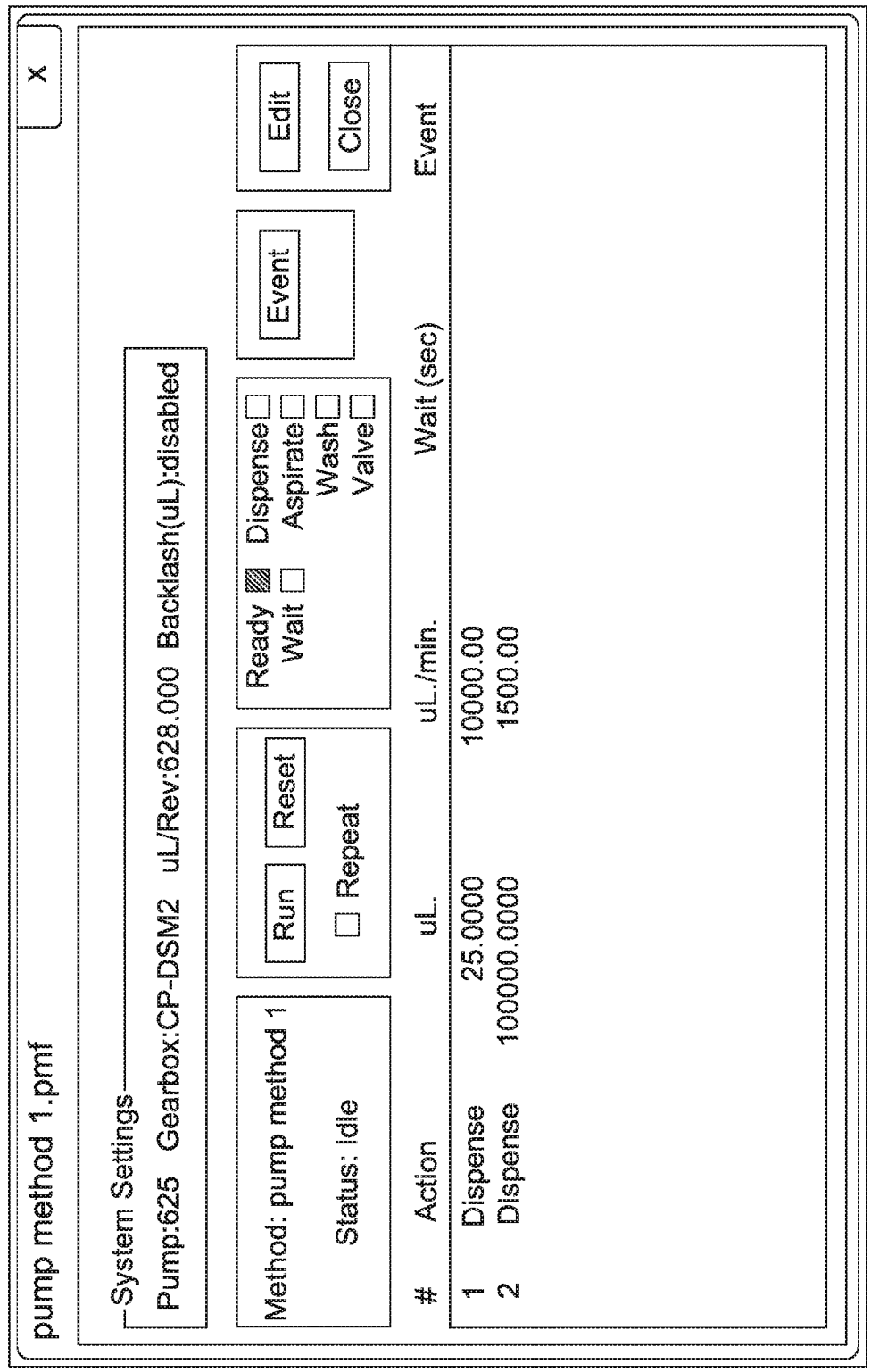
FIG. 16 is an exemplary pump program to pulse the sample delivery to initiate the plasma.

The pump program used to verify this method is shown in FIG. 16. In this method, 25 µL of sample solution is pulsed at a rate of 10 mL/min. This momentarily causes the solution sample 60 to make contact with the anode 30. With the dc power source 20 turned on, the normal operation of the SCGD is then maintained with a sample flow rate of 1.5 mL/min according to the program shown in FIG. 16.

Digital Filtering to Remove High Frequency Noise

Figure 17:
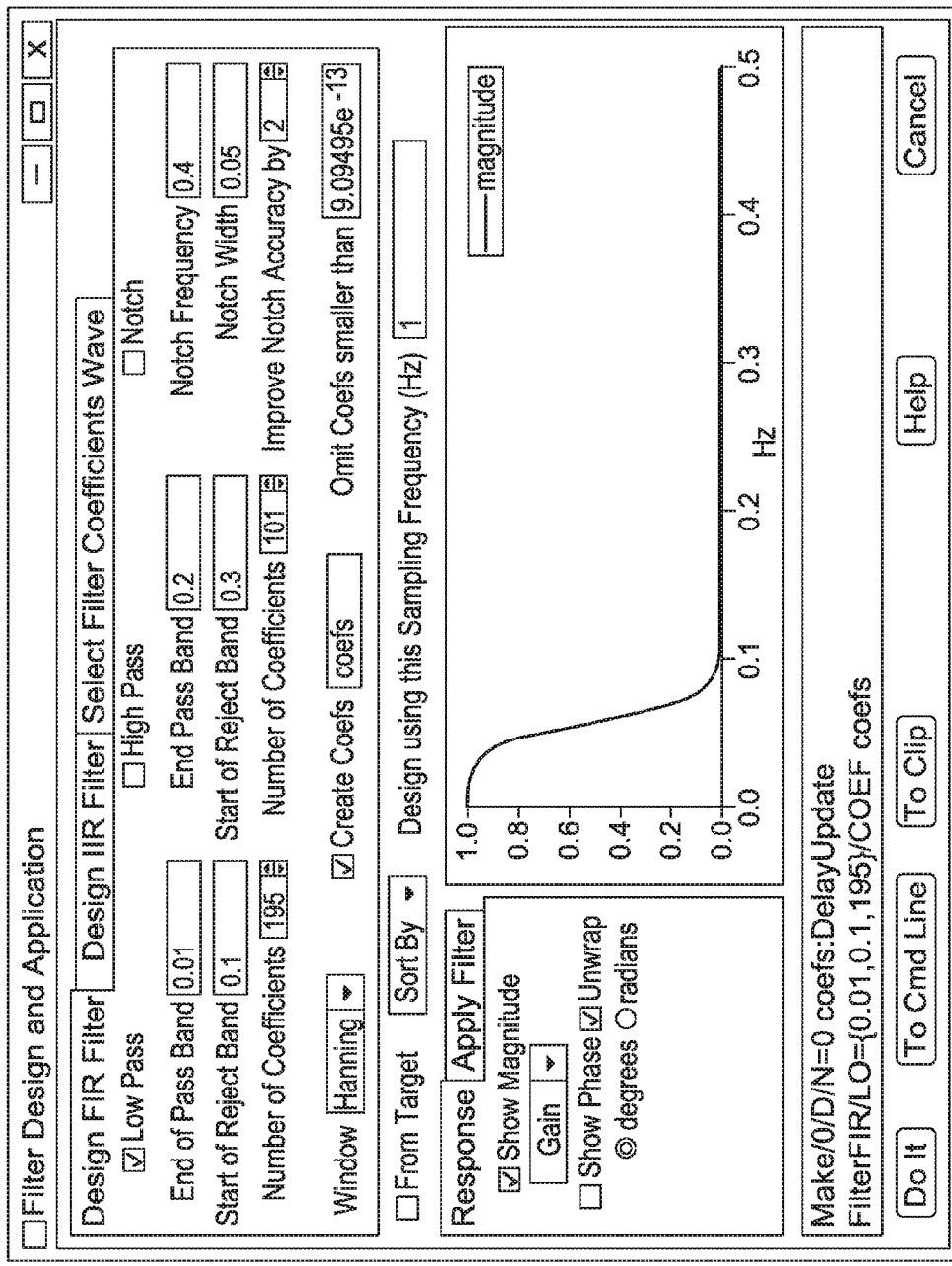
FIG. 17 is an exemplary design criteria for a low pass digital filter.

Prior to calculating the short and long term % rsd values, a low pass digital filter was designed to remove the high frequency noise associated with the emission intensity. The parameters of the low pass digital filter (see FIG. 17) were generated using Igor Pro Version 6.34 A from WaveMetrics.

Use of the Improved SCGD Apparatus for Elemental Analysis

The SCGD may be used to analyze most, if not all, elements of the periodic table. Note that all examples below used an SCGD apparatus with the weir 110 and bubble blocker 120 configuration at a flow rate of 1.5 mL/min.

Spectra from Pure Standards in 0.1 M $HNO_3$

To assess the ability of the SCGD to generate atomic emission signals from elements significant to steam assisted gravity drainage (SAGD) operations, a series of standard solutions were prepared in 0.1 M HNO$_3$. Emission spectra are shown for Mg, Ca, Cu, Al, Fe, Na, Ba, Sr, K, Rb, Cs, and Li in FIGS. 18 to 28. These emission spectra show a strong atomic signal and demonstrate the ability of the SCGD to detect elements of interest for SAGD. The SCGD may also be used to analyze most other elements on the period table.

Figure 18:
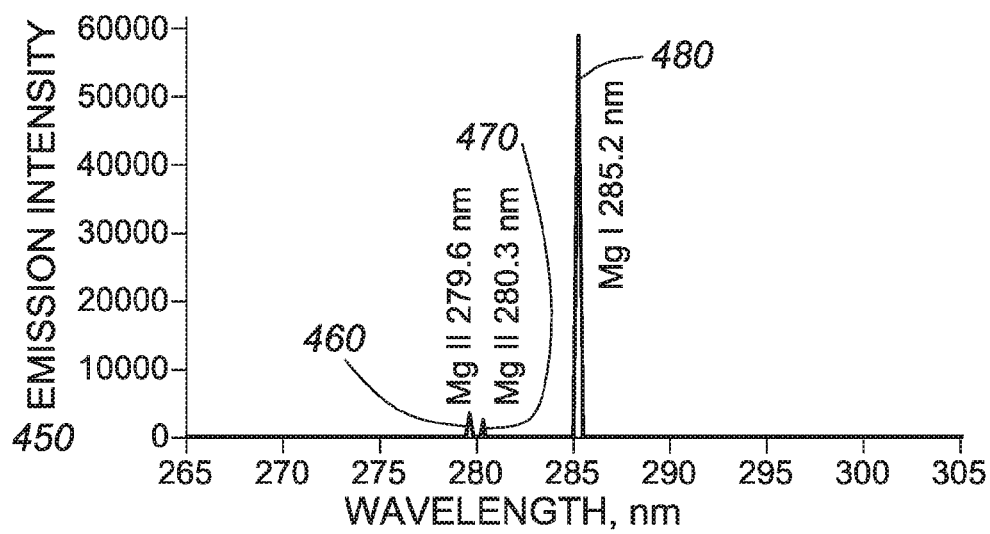
FIG. 18 is a graph of emission intensity for blank subtracted 10 ppm Mg, 80 ms integration, 32 scans averaged.

Referring to FIG. 18, emission intensity 450 indicated readings for Mg II (460) at 279.6 nm, Mg II (470) at 280.3 nm, and Mg I (480) at 285.2 nm.

Figure 19:
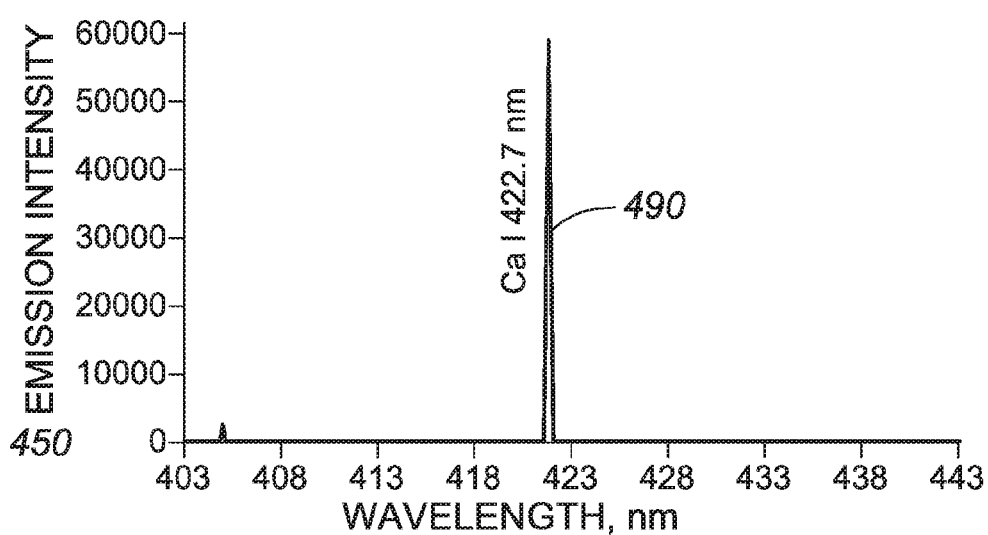
FIG. 19 is a graph of emission intensity for blank subtracted 10 ppm Ca, 1000 ms integration, 32 scans averaged.

Referring to FIG. 19, emission intensity 450 indicated readings for Ca I (490) at 422.7 nm.

Figure 20:
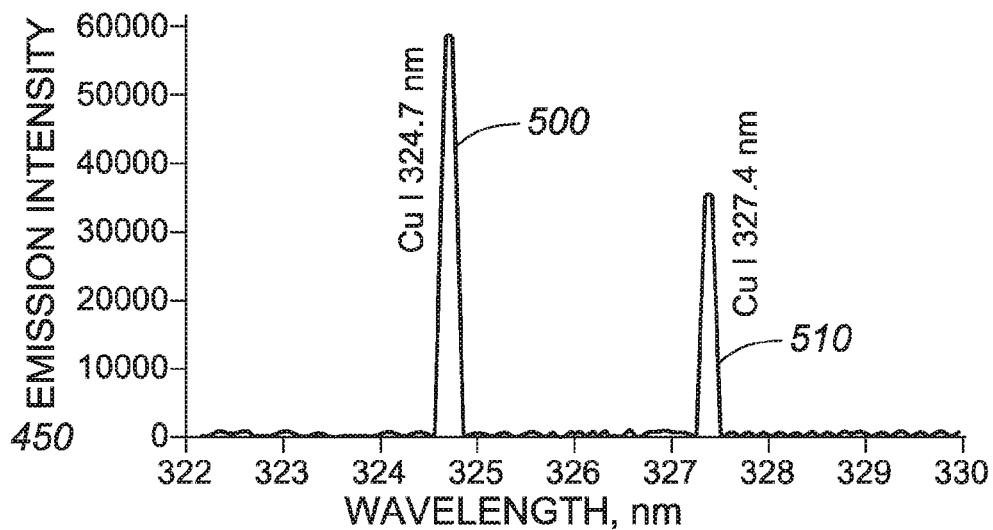
FIG. 20 is a graph of emission intensity for blank subtracted 10 ppm Cu, 230 ms integration, 32 scans averaged.

Referring to FIG. 20, emission intensity 450 indicated readings for Cu I (500) at 324.7 nm and Cu I (510) at 327.7 nm.

Figure 21:
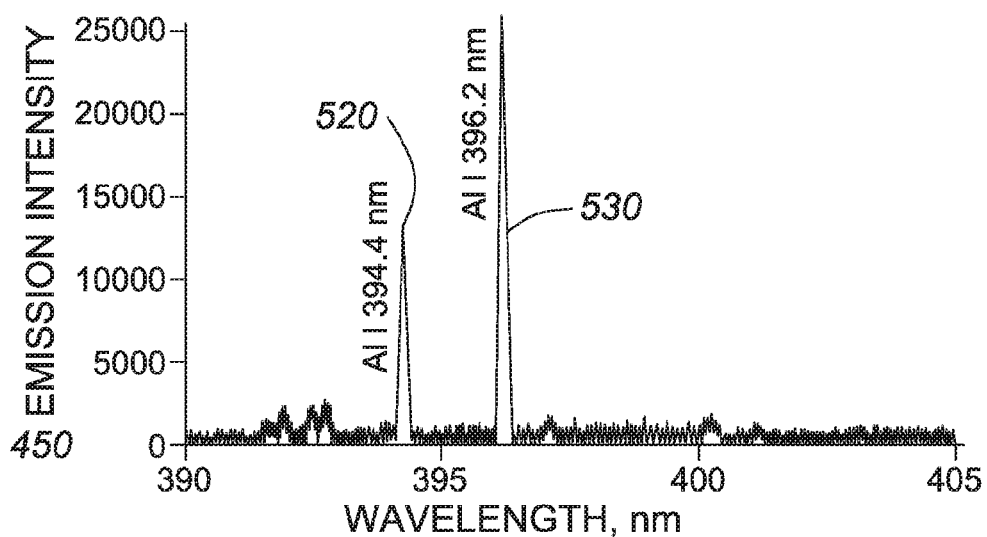
FIG. 21 is a graph of emission intensity for blank subtracted 10 ppm Al, 4550 ms integration, 32 scans averaged.

Referring to FIG. 21, emission intensity 450 indicated readings for Al I (520) at 394.4 nm and Al I (530) at 396.2 nm.

Figure 22:
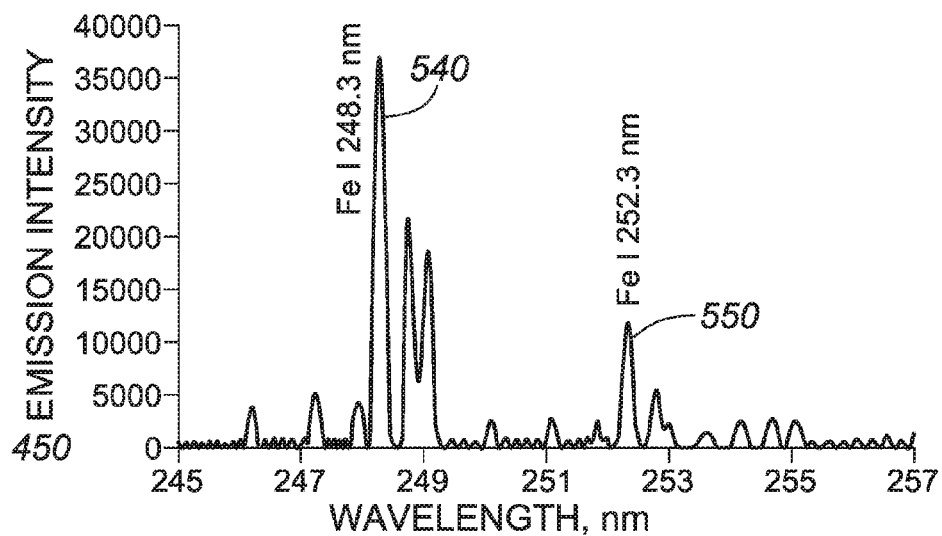
FIG. 22 is a graph of emission intensity for blank subtracted 10 ppm Fe, 4030 ms integration, 32 scans averaged.

Referring to FIG. 22, emission intensity 450 indicated readings for Fe I (540) at 248.3 nm and Fe I (550) at 252.3 nm.

Figure 23:
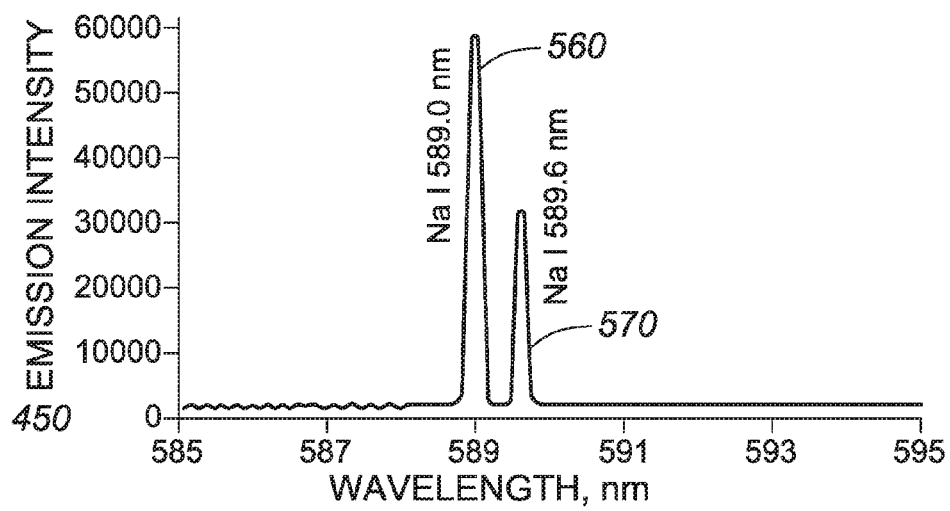
FIG. 23 is a graph of emission intensity for raw Na emission, unknown concentration, 90 ms integration, 32 scans averaged.

Referring to FIG. 23, emission intensity 450 indicated readings for Na I (560) at 589.0 nm and Na I (570) at 589.6 nm.

Figure 24:
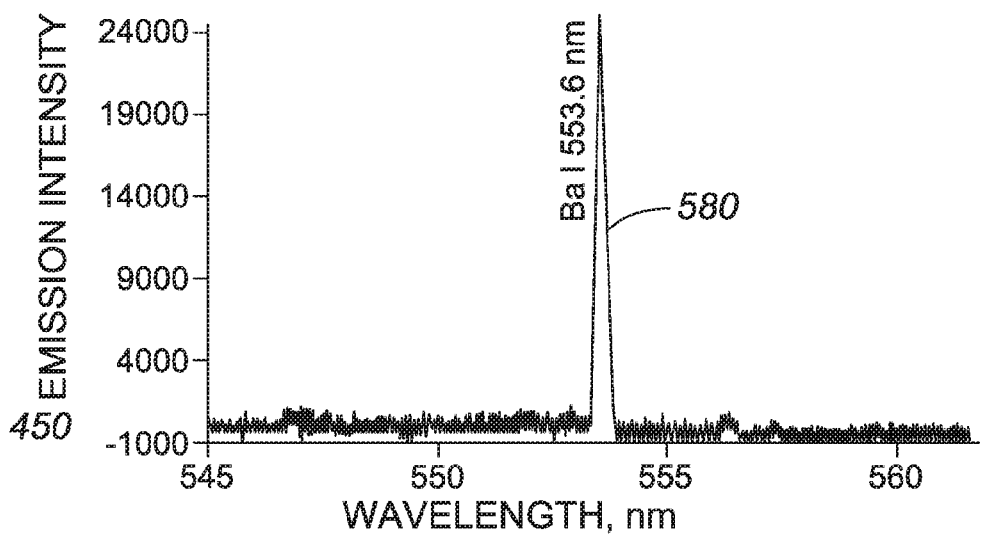
FIG. 24 is a graph of emission intensity for blank subtracted 10 ppm Ba, 6.5 s integration, 32 scans averaged.

Referring to FIG. 24, emission intensity 450 indicated readings for Ba I (580) at 553.6 nm.

Figure 25:
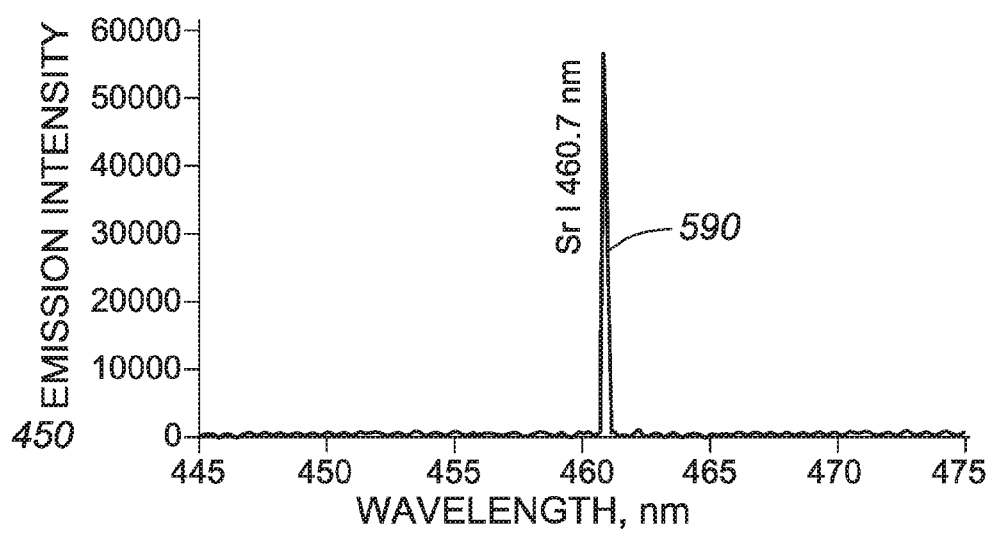
FIG. 25 is a graph of emission intensity for blank subtracted 10 ppm Sr, 2210 ms integration, 32 scans averaged.

Referring to FIG. 25, emission intensity 450 indicated readings for Sr I (590) at 460.7 nm.

Figure 26:
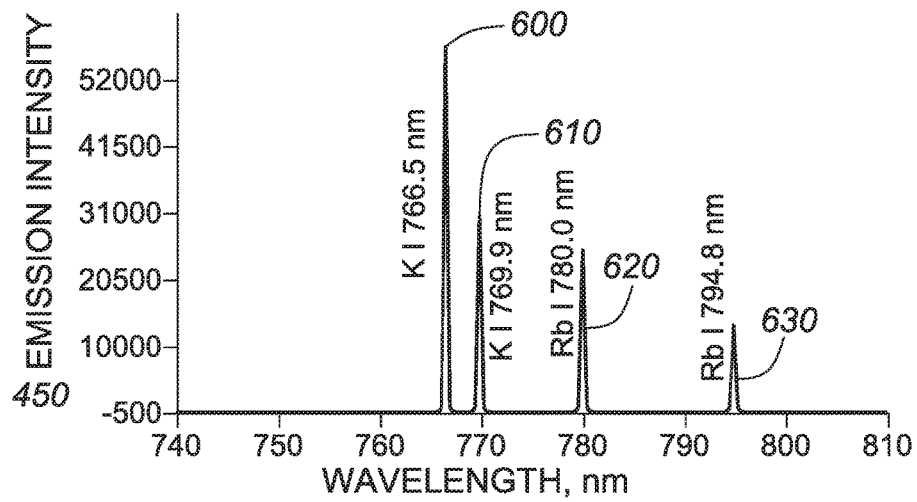
FIG. 26 is a graph of emission intensity for blank subtracted 10 ppm K and Rb, 9.2 ms integration, 32 scans averaged.

Referring to FIG. 26, emission intensity 450 indicated readings for K I (600) at 766.5 nm, K I (610) at 769.9 nm, Rb I (620) at 780.0 nm, and Rb I (630) at 794.8 nm.

Figure 27:
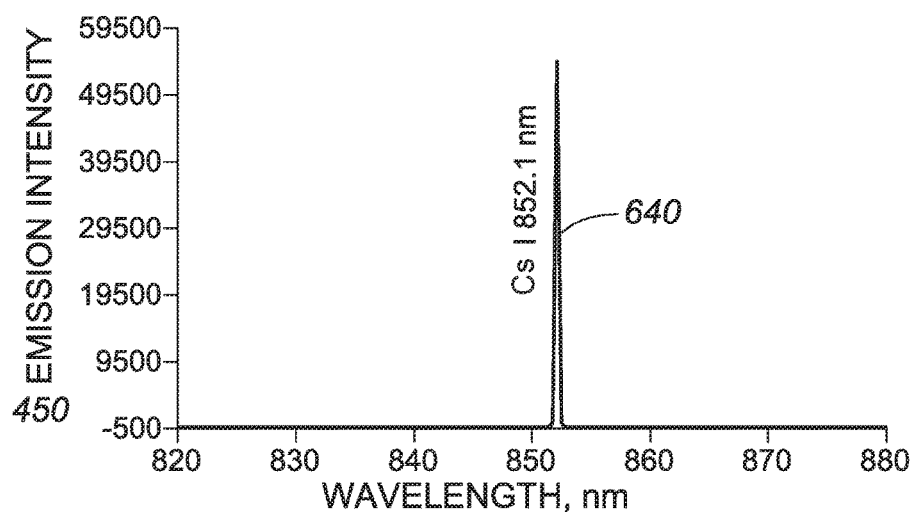
FIG. 27 is a graph of emission intensity for blank subtracted 20 ppm Cs, 65 ms integration, 32 scans averaged.

Referring to FIG. 27, emission intensity 450 indicated readings for Cs I (640) at 852.1 nm.

Figure 28:
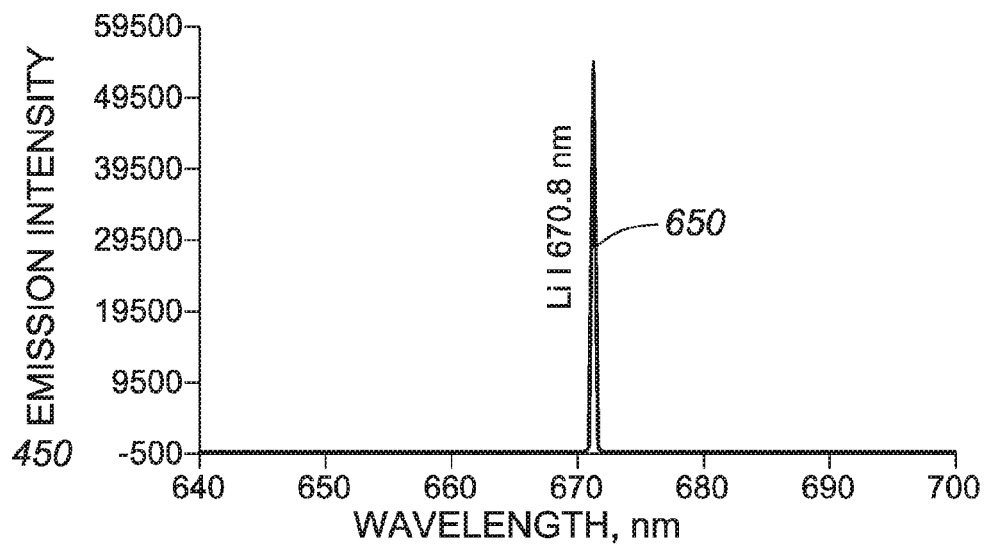
FIG. 28 is a graph of emission intensity for blank subtracted 10 ppm Li, 6 ms integration, 32 scans averaged.

Referring to FIG. 28, emission intensity 450 indicated readings for Li I (650) at 670.8 nm.

Detected Elements from Filtered SAGD Produced Water

A sample of SAGD produced water was filtered, diluted 10:1 and acidified to a pH value of 1 with HNO$_3$. A stable plasma was maintained with this sample matrix and emission was observed from Na, K, Ca, and Li, see FIGS. 29 to 32. Other elements were either not present in the sample or below the instrument detection limits.

Figure 29:
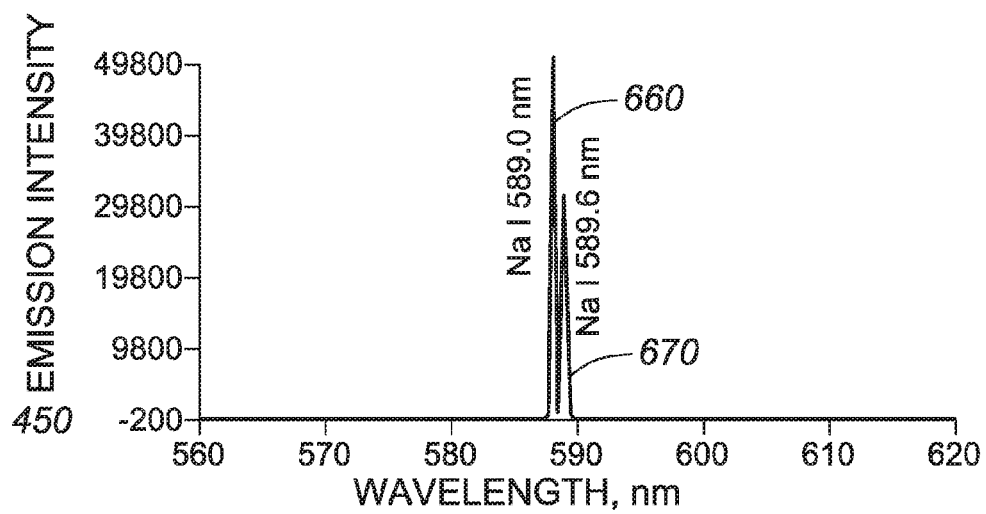
FIG. 29 is a graph of emission intensity for blank subtracted filtered SAGD process water, diluted 10:1, 1.9 ms integration, 32 scans averaged.

Referring to FIG. 29, emission intensity 450 indicated readings for Na I (660) at 589.0 nm and Na I (670) at 589.6 nm.

Figure 30:
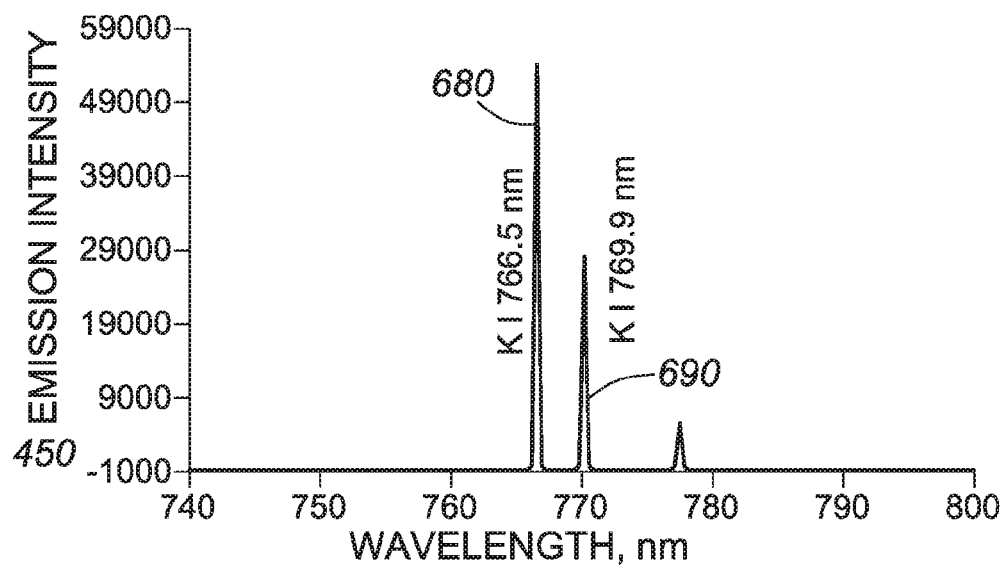
FIG. 30 is a graph of emission intensity for blank subtracted filtered SAGD process water, diluted 10:1, 180 ms integration, 32 scans averaged.

Referring to FIG. 30, emission intensity 450 indicated readings for K I (680) at 766.5 nm and K I (690) at 769.9 nm.

Figure 31:
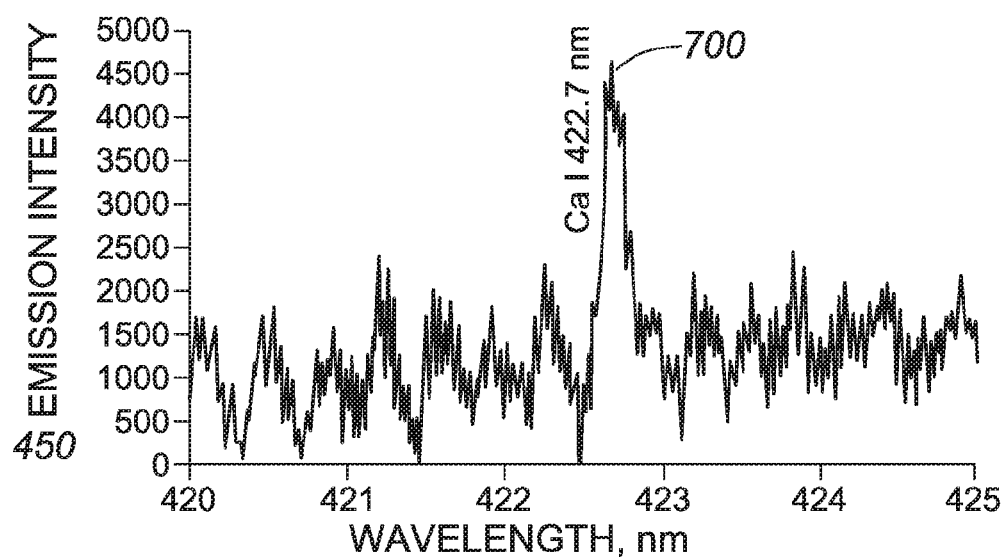
FIG. 31 is a graph of emission intensity for blank subtracted filtered SAGD process water, diluted 10:1, 6.5 s integration, 32 scans averaged.

Referring to FIG. 31, emission intensity 450 indicated readings for Ca I (700) at 422.7 nm.

Figure 32:
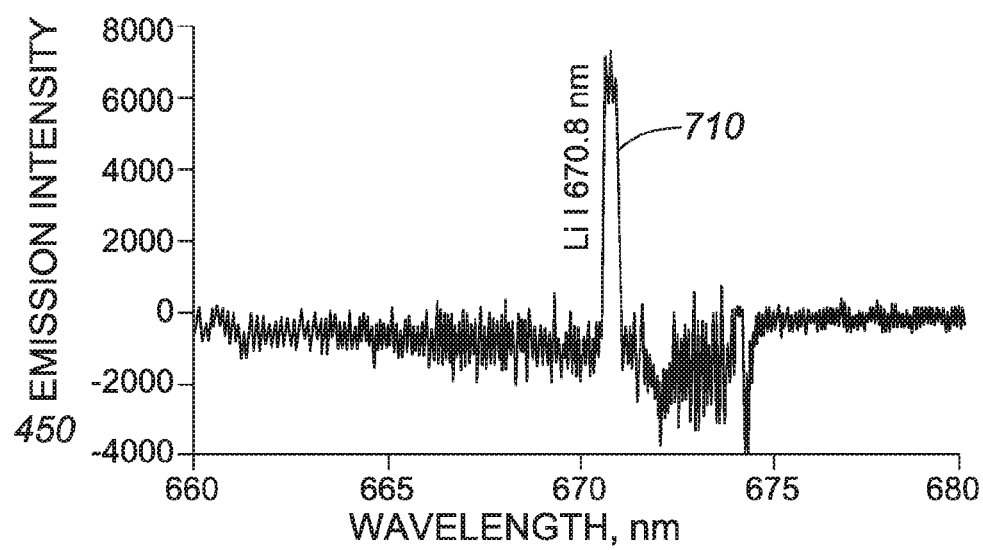
FIG. 32 is a graph of emission intensity for blank subtracted filtered SAGD process water, diluted 10:1, 430 ms integration, 32 scans averaged.

Referring to FIG. 32, emission intensity 450 indicated readings for Li I (710) at 670.8 nm.

Filtered SAGD Produced Water Spiked with Elements of Interest

The same filtered SAGD produced water as used in the previous section was spiked with selected elements to establish the ability of the SCGD to detect elements of interest in a SAGD produced water matrix. Emission spectra of these elements is shown in FIGS. 33 to 42. Results show that the SCGD is capable of detecting the elements of interest for SAGD applications from a SAGD produced water matrix.

Figure 33:
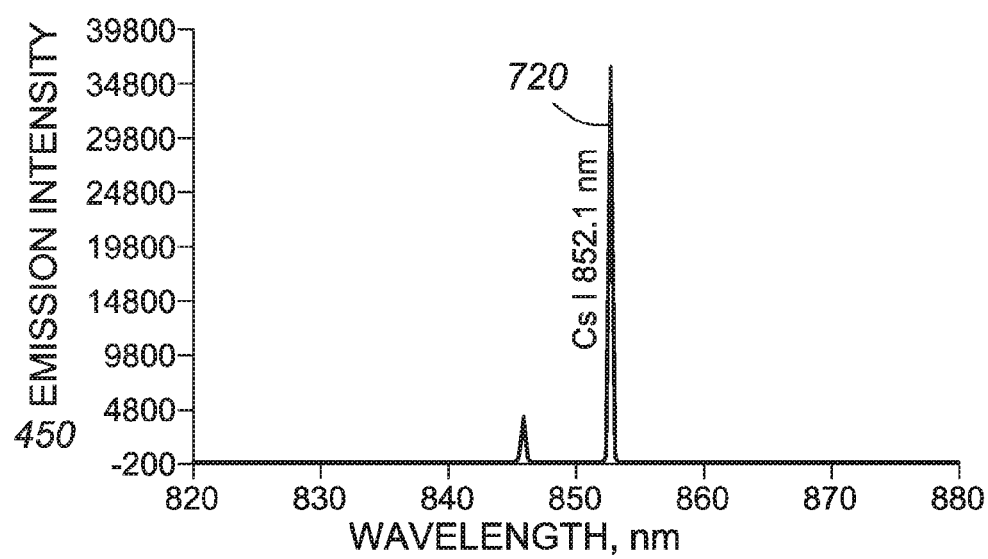
FIG. 33 is a graph of emission intensity for steam assisted gravity drainage (SAGD) produced water solution diluted 10:1 spiked with 10 ppm Cs, 130 ms integration, blank subtracted, 32 scans averaged.

Referring to FIG. 33, emission intensity 450 indicated readings for Cs I (720) at 852.1 nm.

Figure 34:
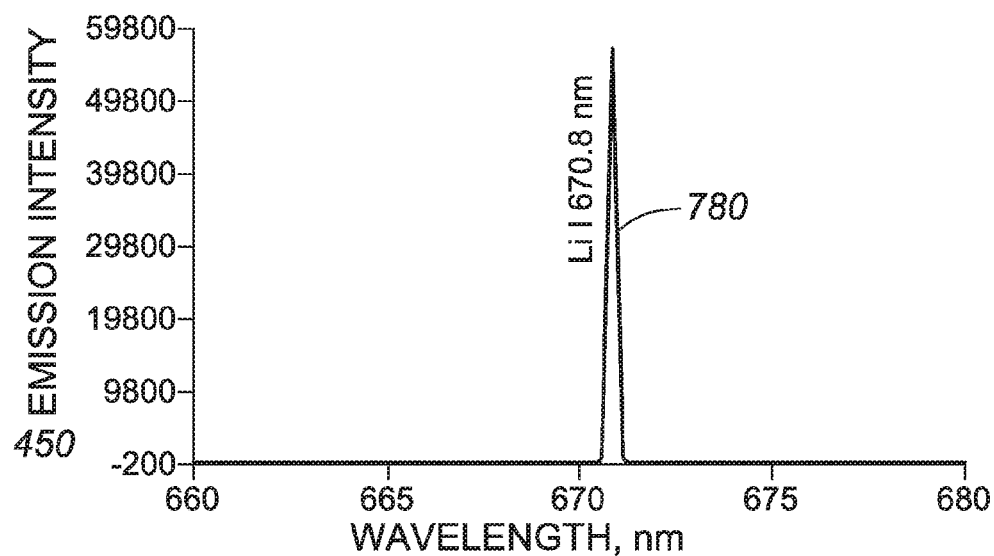
FIG. 34 is a graph of emission intensity for SAGD produced water solution diluted 10:1 spiked with 10 ppm Li, 5.7 ms integration, blank subtracted, 32 scans averaged.

Referring to FIG. 34, emission intensity 450 indicated readings for Li I (730) at 670.8 nm.

Figure 35:
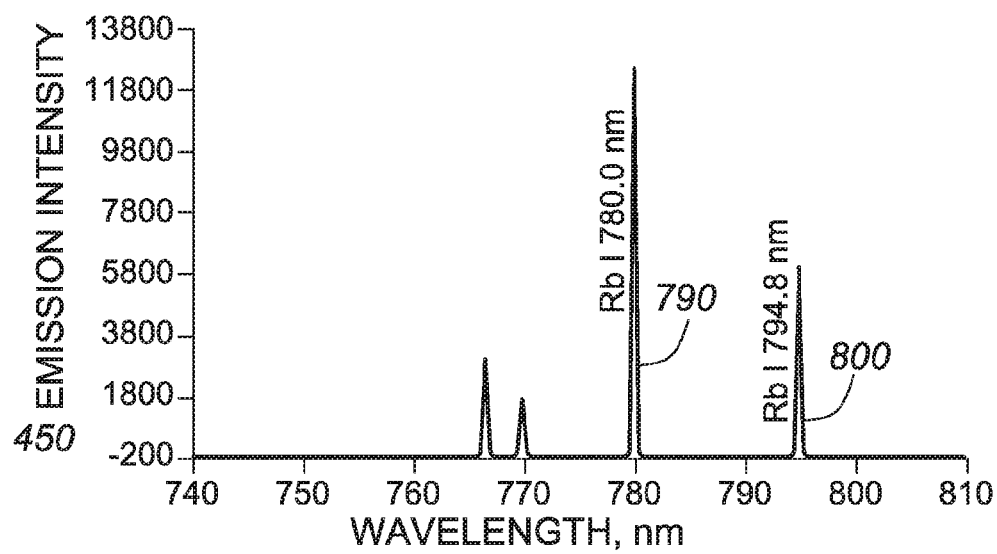
FIG. 35 is a graph of emission intensity for SAGD produced water solution diluted 10:1 spiked with 10 ppm Rb, 9.2 ms integration, blank subtracted, 32 scans averaged.

Referring to FIG. 35, emission intensity 450 indicated readings for Rb I (790) at 780.0 nm and Rb I (800) at 794.8 nm.

Figure 36:
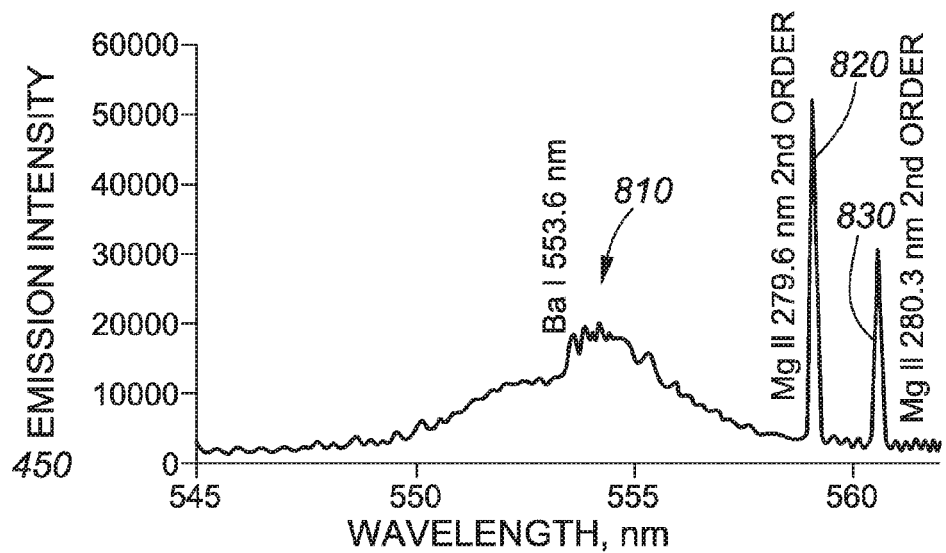
FIG. 36 is a graph of emission intensity for SAGD produced water solution diluted 10:1 spiked with 10 ppm Ba, 6.5 s integration, blank subtracted, 32 scans averaged.

Referring to FIG. 36, emission intensity 450 indicated readings for Ba I (810) at 553.6 nm, Mg II (820) at 279.6 nm $2^{nd}$ order, and Mg II (830) at 280.3 nm $2^{nd}$ order. The Barium (Ba) (810) shows poor emission since Ba is known to precipitate in the presence of sulfate. This precipitation would leave very little dissolved Ba in solution.

Figure 37:
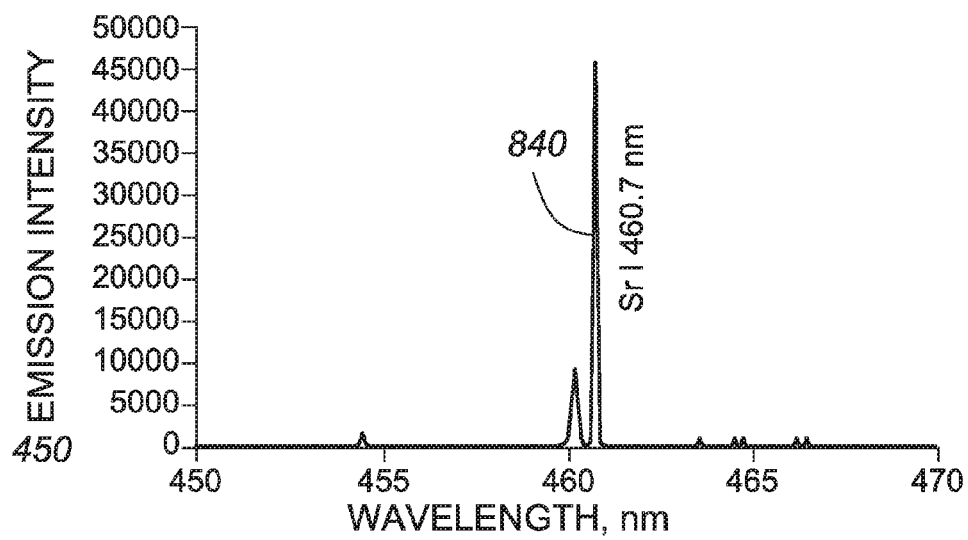
FIG. 37 is a graph of emission intensity for SAGD produced water solution diluted 10:1 spiked with 10 ppm Sr, 3315 ms integration, blank subtracted, 32 scans averaged.

Referring to FIG. 37, emission intensity 450 indicated readings for Sr I (840) at 460.7 nm.

Figure 38:
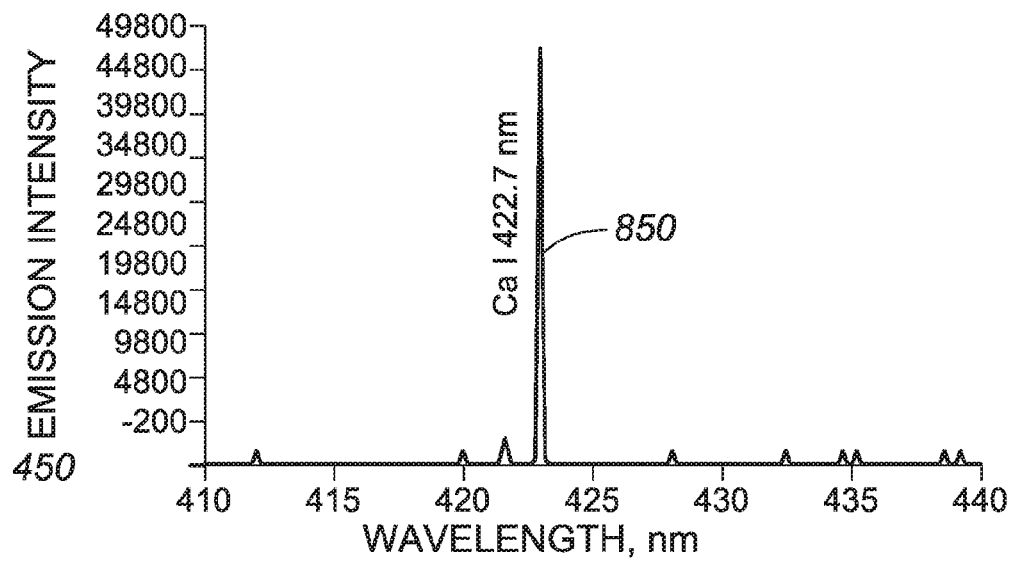
FIG. 38 is a graph of emission intensity for SAGD produced water solution diluted 10:1 spiked with 10 ppm Ca, 1430 ms integration, blank subtracted, 32 scans averaged.

Referring to FIG. 38, emission intensity 450 indicated readings for Ca I (850) at 422.7 nm.

Figure 39:
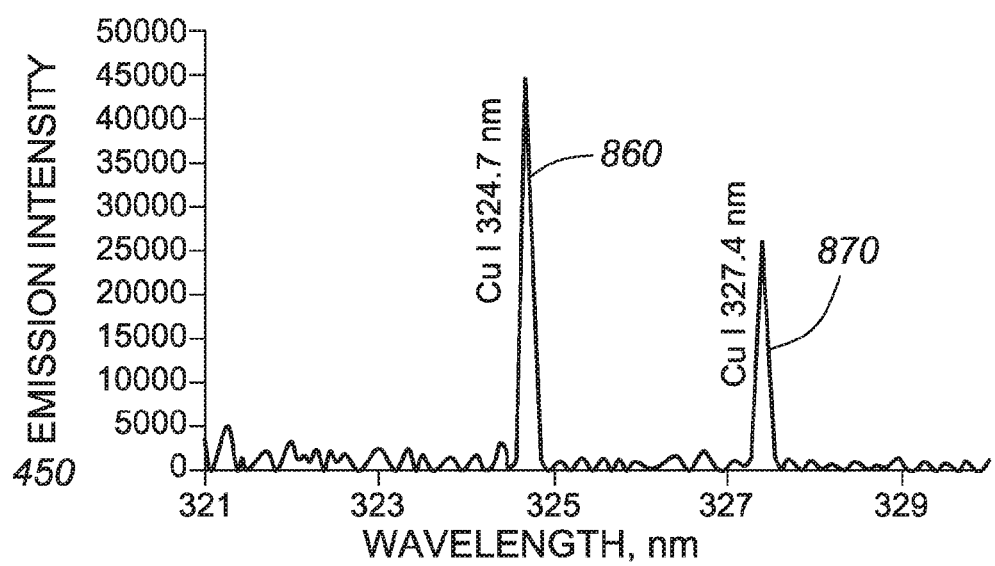
FIG. 39 is a graph of emission intensity for SAGD produced water solution diluted 10:1 spiked with 10 ppm Cu, 170 ms integration time, blank subtracted, 32 scans averaged.

Referring to FIG. 39, emission intensity 450 indicated readings for Cu I (860) at 324.7 nm and Cu I (870) at 327.4 nm.

Figure 40:
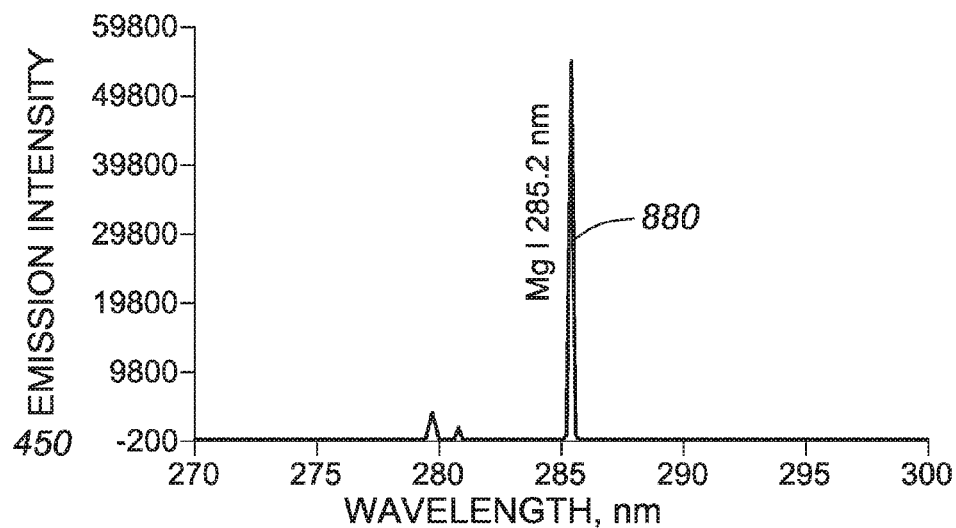
FIG. 40 is a graph of emission intensity for SAGD produced water solution diluted 10:1 spiked with 10 ppm Mg, 150 ms integration time, blank subtracted, 32 scans averaged.

Referring to FIG. 40, emission intensity 450 indicated readings for Mg I (870) at 285.2 nm.

Figure 41:
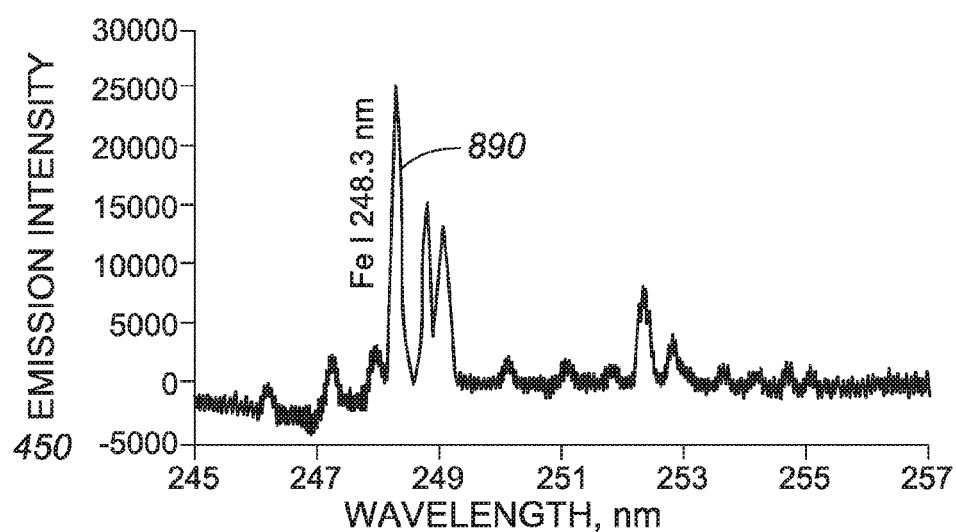
FIG. 41 is a graph of emission intensity for SAGD produced water solution diluted 10:1 spiked with 10 ppm Fe, 4095 ms integration, blank subtracted, 32 scans averaged.

Referring to FIG. 41, emission intensity 450 indicated readings for Fe I (890) at 248.3 nm.

Figure 42:
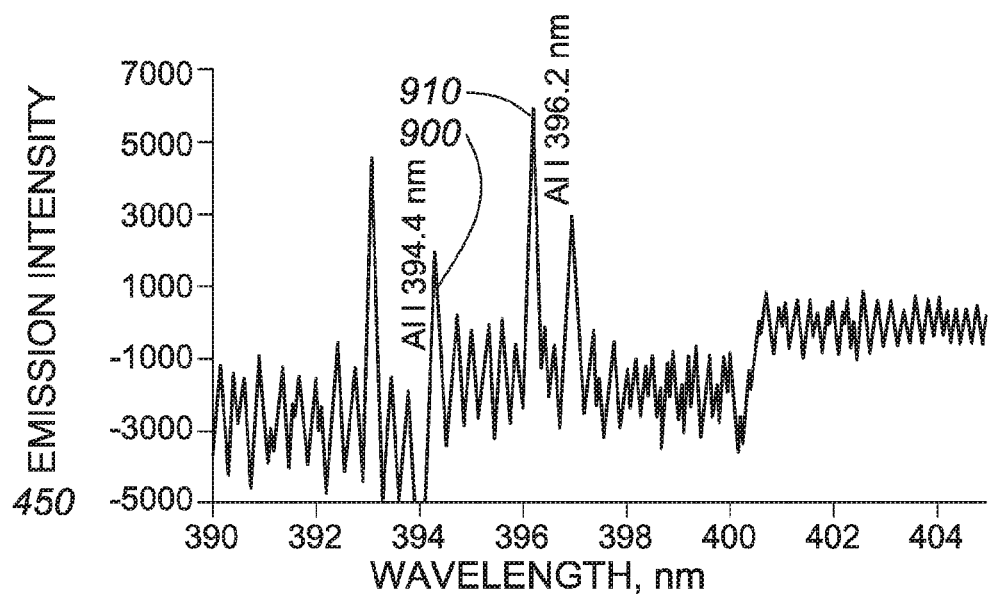
FIG. 42 is a graph of emission intensity for SAGD produced water solution diluted 10:1 spiked with 10 ppm Al, 3640 ms integration, blank subtracted, 32 scans averaged.

Referring to FIG. 42, emission intensity 450 indicated readings for Al I (900) at 394.4 nm and Al I (910) at 396.2 nm.

Measurement of Colloidal Counterions and Estimation of Clay Content

Figure 43:
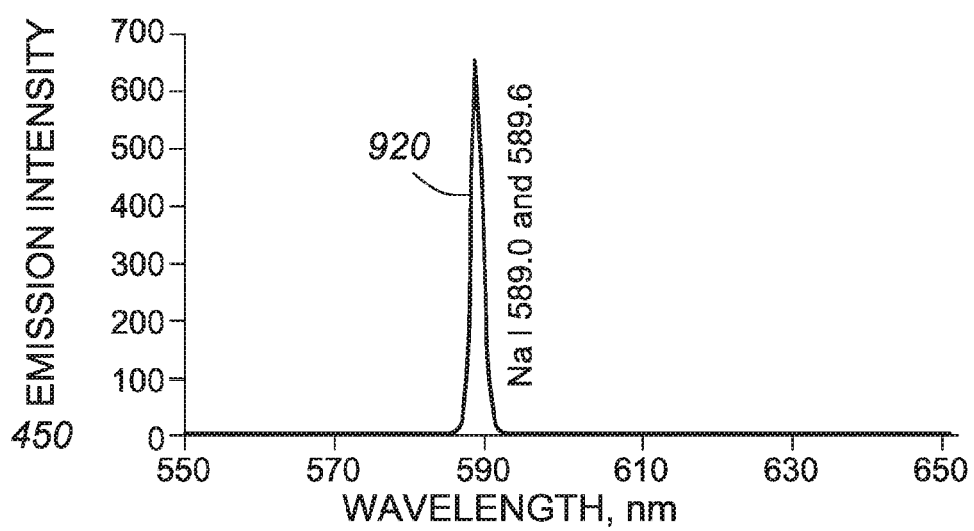
FIG. 43 is a graph of emission intensity for SAGD produced water solution, diluted 100:1, filtered emission subtracted from unfiltered emission, acquired with an Ocean Optics SD2000.

Investigations of filtered and unfiltered SAGD (Steam Assisted Gravity Drainage) process water was made with the SCGD. These results show that the SCGD may be capable of determining both clay content and cations relevant to bitumen extraction. Clay particles of SiAlO$_4$— are negatively charged and therefore attract and retain cations. The relative strength of this attraction is given in the following lyotropic series: $Ca^{2+}>Mg^{2+}>K^+>Na^+$. When a slurry of clay particles is acidified, the release of cations will follow the reverse of the lyotropic series. Results have shown (see FIG. 43) the sodium emission signal of an acidified filtered SAGD sample subtracted from the sodium emission signal from an acidified unfiltered sample may represent an indirect measure of the clay content of the sample and a direct measure of clay counterions released by acidification. Referring to FIG. 43, emission intensity 450 indicated readings for Na I (920) at 589.0 nm and 589.6 nm.

Measurement of Molecular Species

Oxides, nitrides, and hydrides are classes of molecular species that can be formed in atmospheric pressure plasmas and can be detected by molecular emission. In this way, the SCGD may be used to detect molecular species including, but not limited to, the group IVb, Vb, VIb, and VIIb elements of the periodic table. One example is silica (silicon dioxide), as discussed below and shown in FIGS. 44-46. Another example is total organic carbon (TOC), which may me be able to be analyzed through the molecule emission of CO, CN, or CH.

Figure 44:
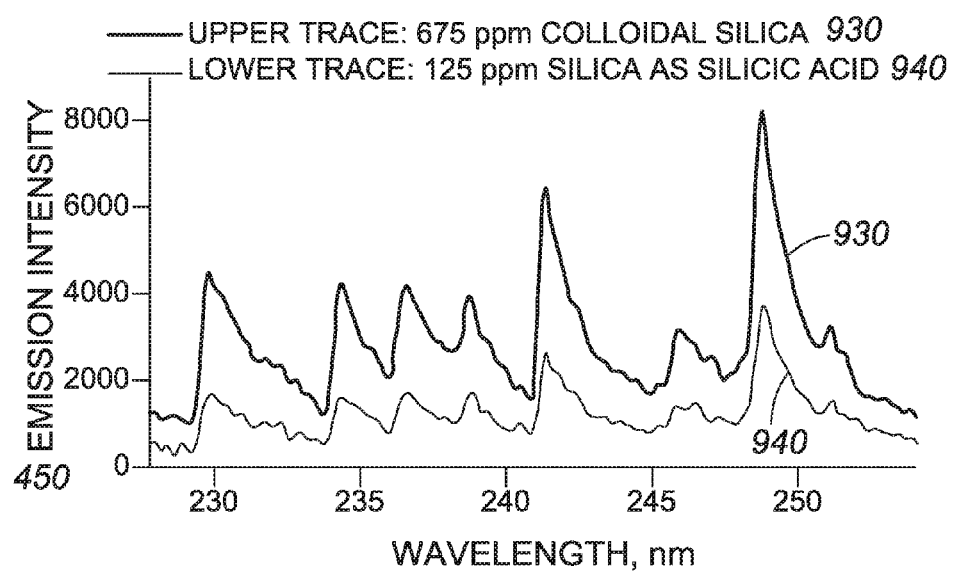
FIG. 44 is a graph of emission intensity for SiO vibrational band emission from 248.7 nm, 241.4 nm, 238.6 nm, 236.7 nm, 234.5 nm, and 229.8 nm from the SCGD plasma emission source.

Emission spectra, FIG. 44, from both colloidal silica 930 and dissolved silica as silicic acid 940 show that the SCGD is capable of generating a signal from silica in the test solution. The emission intensity 450 bands shown in FIG. 44 correspond to literature values of SiO emission according to Motret. (see: Motret, O., et al., *Investigations of silicon oxide UV emission in a non-thermal atmospheric plasma-comparison with synthetic spectra.* Journal of Physics D: Applied Physics, 2003. 36: p. 2060-2066). The plasma emission source used to generate the spectrum shown in the Motret paper is a dielectric barrier discharge (DBD). This DBD is not capable of directly analyzing solution samples and is not an appropriate choice for an online analysis technique.

Figure 45:
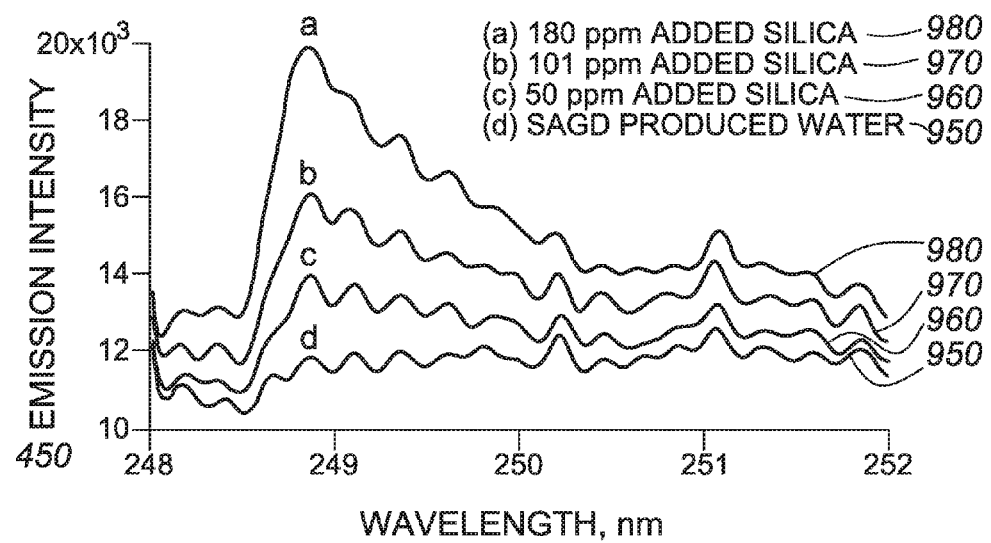
FIG. 45 is a graph of emission intensity for SAGD produced water diluted 10:1 spiked with silica, 6.5 s integration, blank subtracted, 32 scans averaged, low pass digitally filtered.

Silica is an important factor responsible for boiler fouling and scale formation in heat exchangers. To illustrate that the SCGD disclosed herein is capable of determining silica in industrial solutions, an unfiltered produced water SAGD sample was spiked with increasing amounts of silica from silicic acid and emission spectra are shown in FIG. 45. Referring to FIG. 45, emission intensity 450 is shown for SAGD produced water (950), 50 ppm added silica (960), 101 ppm added silica (970), and 180 ppm added silica (980).

Figure 46:
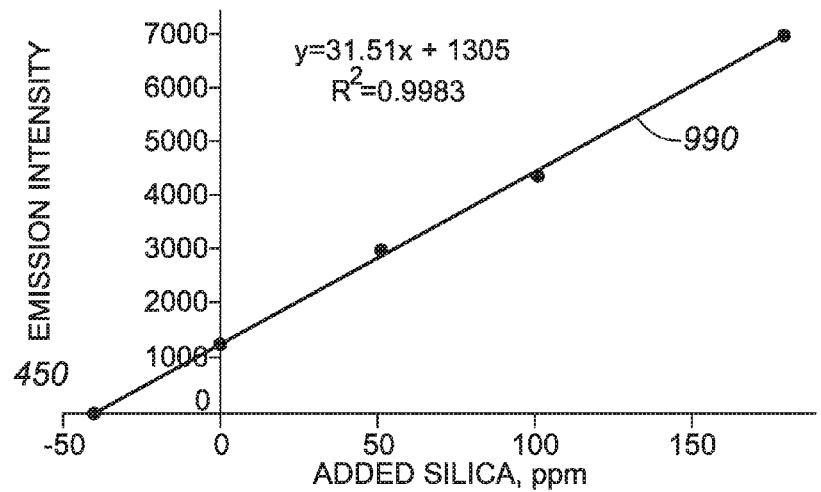
FIG. 46 is a graph of emission intensity for standard addition determination of silica in unfiltered SAGD produced water, signal defined at the emission intensity difference between 248.85 nm and 248.45 nm.

The difference in emission intensity from 248.85 and 248.45 nm is plotted for all concentrations in FIG. 46. The linearity of this calibration curve 990 demonstrates the suitability of the SCGD to accurately determine silica in industrial process solutions. In this example, the calibration curve 990 fits a linear equation: y=31.51x+1035 with $R^2$=0.9983, where x is the added silica in ppm and y is the emission intensity.

In this example, the silica concentration was determined to be 41 mg/L by the method of standard additions. Since the sample was diluted 10:1 prior to analysis, the original concentration of silica in the produced water sample was 410 mg/L.

Molecular Isotopic Spectrometry by SCGD

We have shown, for the first time, that SCGD can be used for isotopic differentiation by the analysis of natural ($H_2O$) water (1000) and heavy ($D_2O$) water (1010). Based on this observation, we predict that the SCGD may be used for additional isotope analyses in the same way as the LAMIS technique.

Figure 47:
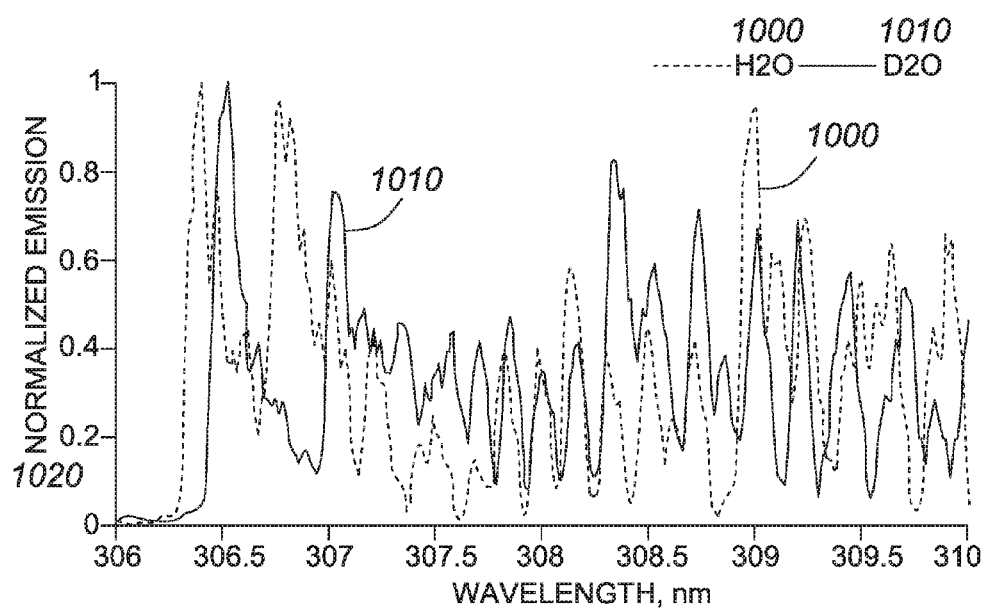
FIG. 47 is a graph of normalized emission spectra of $^{16}OH$ and $^{16}OD$ by the SCGD technique, 32 scans averaged.
Figure 48:
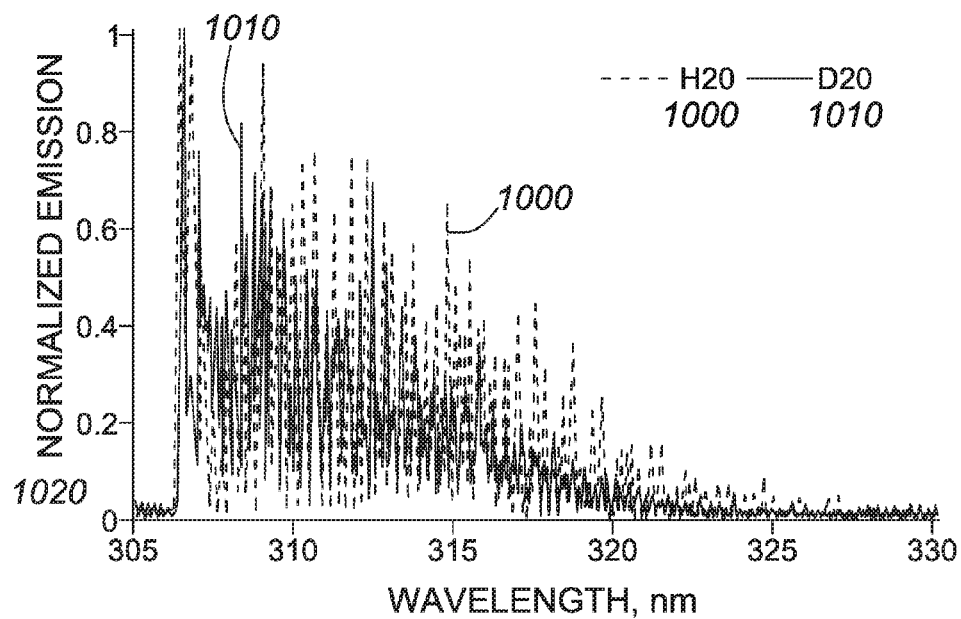
FIG. 48 is a graph of normalized emission spectra of the entire $^{16}OH$ and $^{16}OD$ band head by SCGD.
Figure 49:
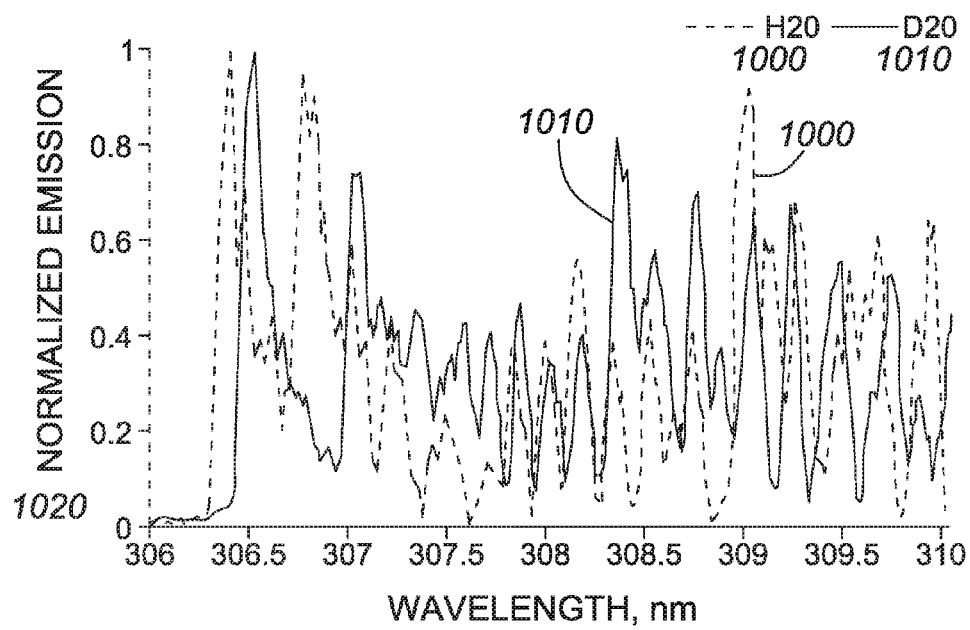
FIG. 49 is a graph of normalized emission spectra of $^{16}OH$ and $^{16}OD$ between 306 and 310 nm by SCGD.

Bol'shakov, A. A. et al. demonstrate how the LAMIS technique can be used to optically differentiate and quantify the isotopes of oxygen and hydrogen through optical spectrometry. In comparison, the spectra 1020 shown in FIG. 47 demonstrate how the SCGD technique produces the same type of spectral signature as the LAMIS technique. This illustrates that the SCGD technique is a complimentary technique compared with LAMIS for stable isotope differentiation. Compared with LAMIS, SCGD is a simpler technique that does not require a pulsed laser and temporal optical detection. The SCGD technique is also much better at solution based analysis as compared with LAMIS. The spectra 1020 shown in FIGS. 48 and 49 show the same 16OH and 16OD band head emission from the SCGD source over different wavelength regions for natural ($H_2O$) water (1000) and heavy ($D_2O$) water (1010). SCGD is predicted to be capable of measuring any isotopes that can be detected by LAMIS techniques including hydrogen, boron, carbon, nitrogen, oxygen, and chlorine.

Preliminary Detection Limits

The disclosed plasma elemental analyzer may be used in a wide variety of applications. In an embodiment disclosed, preliminary detection limits for a plasma elemental analyzer using a SCGD emission cell of the present disclosure are, for example but not limited to, about (in ng/mL or ppb):

| United States Environmental Protection Agency (EPA) Pollutants | |
|---|---|
| Cd | 0.9 |
| Cu | 0.9 |
| Pb | 4 |
| Ni | 2 |
| Ag | 0.2 |
| Tl | 1 |
| Zn | 0.8 |
| Steam Assisted Gravity Drainage (SAGD) | |
| Mg | 0.2 |
| Ca | 0.7 |
| Fe | 3 |
| Al | 8 |
| Mn | 0.7 |

| | |
|---|---|
| Silica | 300 |
| Alkali Metals | |
| Li | 0.005 |
| Na | 0.003 |
| K | 0.004 |
| Rb | 0.007 |
| Cs | 0.2 |
| Other Elemental Analysis Applications | |
| In | 0.2 |
| Ga | 0.6 |

Additional Remarks

All references/citations herein are hereby incorporated by reference.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A solution cathode glow discharge (SCGD) apparatus comprising:
    an anode adapted to connect to a dc power source, the anode having an anode tip;
    a grounding electrode adapted to connect to the dc power source, the grounding electrode having a grounding electrode tip proximate the anode, the region proximate the grounding electrode tip and the anode tip forming a plasma emission region;
    a capillary tube adapted to receive a solution sample, the capillary tube having an outlet tip proximate the grounding electrode tip; and
    a solution-catching collar between the outlet tip of the capillary tube and a base of the grounding electrode tip, adapted to maintain a solution level proximate the plasma emission region.

2. The SCGD apparatus of claim 1, the solution-catching collar comprising a circular weir.

3. The SCGD apparatus of claim 2, further comprising a circular bubble blocker, proximate the outlet tip of the capillary tube to prevent bubbles from directly entering the plasma emission region.

4. The SCGD apparatus of claim 2, the solution-catching collar situated between about 0.3 and 3.0 mm below the outlet tip of the capillary tube.

5. The SCGD apparatus of claim 1, the solution-catching collar comprising a wicking element.

6. The SCGD apparatus of claim 5, the wicking element comprising a glass frit wick or a porous ceramic wick.

7. The SCGD apparatus of claim 6, wherein the wick is disk shaped.

8. The SCGD apparatus of claim 6, wherein the wick is tapered, having a wick tip proximate the grounding electrode tip.

9. The SCGD apparatus of claim 5, further comprising an annular flow restrictor around the grounding electrode such that, in operation, a region of the grounding electrode is substantially covered by waste sample solution.

10. The SCGD apparatus of claim 9, the annular flow restrictor comprising an O-ring or a secondary wicking element.

11. The SCGD apparatus of claim 1, wherein the anode and the grounding electrode are fixed, the distance between the anode tip and the grounding electrode tip set in advance of operation.

12. The SCGD apparatus of claim 1, further comprising a thermally conductive copper heat sink thermally connected with the anode to dissipate heat from the anode.

13. A method of analyzing a solution sample comprising:
providing the solution cathode glow discharge (SCGD) apparatus of claim 1;
providing the solution sample to the capillary tube of the SCGD apparatus at a sampling flow rate less than 2.0 mL/min;
initiating or maintaining a stable plasma glow discharge by applying an electrical current; and
analyzing the glow discharge emission.

14. The method of claim 13, wherein the solution catching collar is a circular weir.

15. The method of claim 13, wherein the solution catching collar is a wicking element.

16. The method of claim 15, the SCGD apparatus further comprising an annular flow restrictor around the grounding electrode such that, in operation, a region of the grounding electrode is substantially covered by waste sample solution.

17. The method of claim 13, wherein the sampling flow rate is about 1.5 mL/min.

18. The method of claim 13, wherein the step of initiating the stable plasma glow discharge comprises pulsing the solution sample at an initiation flow rate, the initiation flow rate greater than the sampling flow rate.

19. The method of claim 18, further comprising contacting an anode of the SCGD apparatus with the solution sample during the initiating.

20. The method of claim 13, conducted online or continuous or in a real-time environment.

21. The method of claim 13, wherein the step of analyzing the glow discharge emission comprises applying a low pass filter to remove high frequency noise.

22. The method of claim 13, wherein the step of analyzing the glow discharge emission comprises detecting one or more molecular species.

23. The method of claim 22, further comprising differentiating isotopes of the one or more molecular species.

24. The method of claim 23, wherein the one or more molecular species are dissolved silica or colloidal silica.

25. A method of measuring colloidal counterions in an acidified solution sample containing clay, the method comprising:
providing a solution cathode glow discharge (SCGD) apparatus;
providing an unfiltered solution sample to a capillary tube of the SCGD;
initiating or maintaining a plasma glow discharge by applying an electrical current; and
detecting at least the sodium glow discharge emission from the unfiltered solution sample;
providing a filtered solution sample to the capillary tube, the filtered solution sample being substantially free from clay;
initiating or maintaining a plasma glow discharge by applying an electrical current; and
detecting at least the sodium glow discharge emission from the filtered solution sample;
subtracting the sodium glow discharge emission of the filtered solution sample from the sodium glow discharge emission of the unfiltered solution sample to indicate a measure of clay counterions released by acidification.

26. The method of claim 25, wherein the net sodium glow discharge emission indicates a relative clay content of the solution sample.

27. The method of claim 25, wherein the SCGD apparatus comprises the SCGD apparatus of claim 1.

* * * * *